US012599326B2

(12) United States Patent
Bishay et al.

(10) Patent No.: US 12,599,326 B2
(45) Date of Patent: *Apr. 14, 2026

(54) MOISTURE-RESISTANT ELECTROCARDIOGRAPHY MONITOR

(71) Applicant: Bardy Diagnostics, Inc., Bellevue, WA (US)

(72) Inventors: Jon Mikalson Bishay, Lexington, KY (US); Jason Felix, Vashon Island, WA (US); Gust H. Bardy, Carnation, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/212,310

(22) Filed: May 19, 2025

(65) Prior Publication Data

US 2025/0281097 A1 Sep. 11, 2025

Related U.S. Application Data

(63) Continuation of application No. 19/098,670, filed on Apr. 2, 2025, now Pat. No. 12,324,672, which is a
(Continued)

(51) Int. Cl.
*A61B 5/05* (2021.01)
*A61B 5/00* (2006.01)
(Continued)

(52) U.S. Cl.
CPC ............ *A61B 5/259* (2021.01); *A61B 5/0006* (2013.01); *A61B 5/0205* (2013.01); *A61B 5/28* (2021.01);
(Continued)

(58) Field of Classification Search
CPC ..... A61B 5/0006; A61B 5/282; A61B 5/1118; A61B 2560/0412; A61B 5/25;
(Continued)

(56) References Cited

U.S. PATENT DOCUMENTS 3,215,136 A 11/1965 Holter et al.
3,569,852 A 3/1971 Berkovits
(Continued)

FOREIGN PATENT DOCUMENTS

CA 2535502 3/2005
CA 2651203 8/2007
(Continued)

OTHER PUBLICATIONS

US 6,527,714 B2, 03/2003, Bardy (withdrawn)
(Continued)

*Primary Examiner* — Joseph A Stoklosa
*Assistant Examiner* — Brian M Antiskay
(74) *Attorney, Agent, or Firm* — K&L Gates LLP

(57) ABSTRACT

Physiological monitoring can be provided through a lightweight wearable monitor that includes two components, a flexible extended wear electrode patch and a reusable monitor recorder that removably snaps into a receptacle on the electrode patch. The wearable monitor sits centrally on the patient's chest along the sternum oriented top-to-bottom. The placement of the wearable monitor in a location at the sternal midline, with its unique narrow "hourglass"-like shape, significantly improves the ability of the wearable monitor to cutaneously sense cardiac electrical potential signals, particularly the P-wave and the QRS interval signals indicating ventricular activity in the ECG waveforms. In particular, the ECG electrodes on the electrode patch are tailored to be positioned axially along the midline of the sternum for capturing action potential propagation in an
(Continued)

orientation that corresponds to the aVF lead used in a conventional 12-lead ECG that is used to sense positive or upright P-waves.

20 Claims, 15 Drawing Sheets

Related U.S. Application Data continuation of application No. 18/318,641, filed on May 16, 2023, now Pat. No. 12,285,261, which is a continuation of application No. 17/959,174, filed on Oct. 3, 2022, now Pat. No. 11,653,869, which is a continuation of application No. 16/782,951, filed on Feb. 5, 2020, now Pat. No. 11,457,852, which is a continuation of application No. 16/404,562, filed on May 6, 2019, now Pat. No. 10,561,328, which is a continuation of application No. 16/174,122, filed on Oct. 29, 2018, now Pat. No. 10,278,606, which is a continuation of application No. 15/645,708, filed on Jul. 10, 2017, now Pat. No. 10,111,601, which is a continuation of application No. 14/488,230, filed on Sep. 16, 2014, now Pat. No. 9,700,227, which is a continuation-in-part of application No. 14/080,725, filed on Nov. 14, 2013, now Pat. No. 9,730,593.

(60) Provisional application No. 61/882,403, filed on Sep. 25, 2013.

(51) Int. Cl.

| | |
|---|---|
| *A61B 5/0205* | (2006.01) |
| *A61B 5/259* | (2021.01) |
| *A61B 5/28* | (2021.01) |
| *A61B 5/282* | (2021.01) |
| *A61B 5/353* | (2021.01) |

(52) U.S. Cl.
CPC .............. *A61B 5/282* (2021.01); *A61B 5/353* (2021.01); *A61B 5/6823* (2013.01); *A61B 5/7225* (2013.01); *A61B 2560/0406* (2013.01); *A61B 2560/0443* (2013.01)

(58) Field of Classification Search
CPC ....... A61B 5/318; A61B 5/332; A61B 5/6833; A61B 5/259; A61B 5/6823
USPC ....... 600/372, 382, 384, 386, 388, 390–393, 600/508–509
See application file for complete search history.

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 3,943,918 A | 3/1976 | Lewis |
| 3,986,495 A | 10/1976 | Miller |
| 3,993,049 A | 11/1976 | Kater |
| 4,123,785 A | 10/1978 | Cherry et al. |
| 4,151,513 A | 4/1979 | Menken et al. |
| 4,328,814 A | 5/1982 | Arkans |
| 4,365,634 A | 12/1982 | Bare et al. |
| 4,441,500 A | 4/1984 | Sessions et al. |
| 4,506,678 A | 3/1985 | Russell et al. |
| 4,532,934 A | 8/1985 | Kelen |
| 4,546,342 A | 10/1985 | Weaver et al. |
| 4,550,502 A | 11/1985 | Grayzel |
| 4,559,953 A | 12/1985 | Wright et al. |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,763,660 A | 8/1988 | Kroll et al. |
| 4,788,983 A | 12/1988 | Brink et al. |
| 4,795,516 A | 1/1989 | Strand |
| 4,809,705 A | 3/1989 | Ascher |
| 4,915,656 A | 4/1990 | Alferness |
| 4,951,672 A | 8/1990 | Buchwald et al. |
| 5,007,429 A | 4/1991 | Treatch et al. |
| 5,025,794 A | 6/1991 | Albert et al. |
| 5,038,782 A | 8/1991 | Gevins et al. |
| 5,093,036 A | 3/1992 | Shafe et al. |
| 5,107,480 A | 4/1992 | Naus |
| 5,168,876 A | 12/1992 | Quedens et al. |
| 5,169,679 A | 12/1992 | Palanisamy |
| 5,195,523 A | 3/1993 | Cartmell et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,312,446 A | 5/1994 | Holschbach et al. |
| 5,314,453 A | 5/1994 | Jeutter |
| 5,331,966 A | 7/1994 | Bennett et al. |
| 5,333,615 A | 8/1994 | Craelius et al. |
| 5,337,748 A | 8/1994 | McAdams et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sandford et al. |
| 5,458,141 A | 10/1995 | Neil |
| 5,473,537 A | 12/1995 | Glazer et al. |
| 5,479,922 A | 1/1996 | Reichl |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,665,477 A | 9/1997 | Meathrel et al. |
| 5,676,559 A | 10/1997 | Laub et al. |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olson et al. |
| 5,788,633 A | 8/1998 | Mahoney |
| 5,817,151 A | 10/1998 | Olson et al. |
| 5,819,741 A | 10/1998 | Karlsson et al. |
| 5,850,920 A | 12/1998 | Gilman et al. |
| 5,860,918 A | 1/1999 | Schradi et al. |
| 5,862,803 A | 1/1999 | Besson et al. |
| D407,159 S | 3/1999 | Roberg |
| 5,876,351 A | 3/1999 | Rohde |
| 5,906,583 A | 5/1999 | Rogel |
| 5,913,829 A | 6/1999 | Reeves et al. |
| 5,919,155 A | 7/1999 | Lattin et al. |
| 5,944,662 A | 8/1999 | Schoendorfer |
| 5,951,598 A | 9/1999 | Bishay et al. |
| 5,956,013 A | 9/1999 | Raj et al. |
| 5,957,857 A | 9/1999 | Hartley |
| 5,984,102 A | 11/1999 | Tay |
| 5,987,352 A | 11/1999 | Klein et al. |
| 5,995,861 A | 11/1999 | Price |
| 6,032,064 A | 2/2000 | Devlin et al. |
| 6,038,469 A | 3/2000 | Karlsson et al. |
| 6,101,413 A | 8/2000 | Olson et al. |
| 6,115,638 A | 9/2000 | Groenke |

(56)        References Cited

U.S. PATENT DOCUMENTS

| | | | |
|---|---|---|---|
| 6,117,077 | A | 9/2000 | Del Mar et al. |
| 6,134,479 | A | 10/2000 | Brewer et al. |
| 6,148,233 | A | 11/2000 | Owen et al. |
| 6,149,602 | A | 11/2000 | Arcelus |
| 6,149,781 | A | 11/2000 | Forand |
| 6,185,452 | B1 | 2/2001 | Schulman et al. |
| 6,188,407 | B1 | 2/2001 | Smith et al. |
| 6,223,080 | B1 | 4/2001 | Thompson |
| D443,063 | S | 5/2001 | Pisani et al. |
| 6,229,098 | B1 | 5/2001 | Dunn et al. |
| 6,238,338 | B1 | 5/2001 | DeLuca et al. |
| 6,245,025 | B1 | 6/2001 | Torok et al. |
| 6,246,330 | B1 | 6/2001 | Nielsen |
| 6,249,696 | B1 | 6/2001 | Olson et al. |
| D445,507 | S | 7/2001 | Pisani et al. |
| 6,267,723 | B1 | 7/2001 | Matsumura et al. |
| 6,269,267 | B1 | 7/2001 | Bardy et al. |
| 6,272,385 | B1 | 8/2001 | Bishay et al. |
| 6,289,238 | B1 | 9/2001 | Besson et al. |
| 6,298,255 | B1 | 10/2001 | Cordero et al. |
| 6,301,502 | B1 | 10/2001 | Owen et al. |
| 6,304,773 | B1 | 10/2001 | Taylor et al. |
| 6,304,780 | B1 | 10/2001 | Owen et al. |
| 6,304,783 | B1 | 10/2001 | Lyster et al. |
| 6,322,532 | B1 | 11/2001 | D'Sa et al. |
| 6,341,230 | B1 | 1/2002 | Koike et al. |
| 6,374,138 | B1 | 4/2002 | Owen et al. |
| 6,381,482 | B1 | 4/2002 | Jayaraman et al. |
| 6,416,471 | B1 | 7/2002 | Kumar et al. |
| 6,418,342 | B1 | 7/2002 | Owen et al. |
| 6,424,860 | B1 | 7/2002 | Karlsson et al. |
| 6,427,083 | B1 | 7/2002 | Owen et al. |
| 6,427,085 | B1 | 7/2002 | Boon et al. |
| 6,434,410 | B1 | 8/2002 | Cordero |
| 6,450,845 | B1 | 9/2002 | Snyder et al. |
| 6,454,708 | B1 | 9/2002 | Ferguson et al. |
| 6,456,256 | B1 | 9/2002 | Amundson et al. |
| 6,456,872 | B1 | 9/2002 | Faisandier |
| 6,463,320 | B1 | 10/2002 | Xue et al. |
| 6,469,669 | B1 | 10/2002 | Tran |
| 6,494,829 | B1 | 12/2002 | New, Jr. et al. |
| 6,505,069 | B2 | 1/2003 | Scott et al. |
| 6,546,285 | B1 | 4/2003 | Owen et al. |
| 6,605,046 | B1 | 8/2003 | Del Mar |
| 6,607,485 | B2 | 8/2003 | Bardy |
| 6,611,705 | B2 | 8/2003 | Hopman et al. |
| 6,623,312 | B2 | 9/2003 | Merry et al. |
| 6,671,545 | B2 | 12/2003 | Fincke |
| 6,671,547 | B2 | 12/2003 | Lyster et al. |
| 6,694,186 | B2 | 2/2004 | Bardy |
| 6,704,595 | B2 | 3/2004 | Bardy |
| 6,705,991 | B2 | 3/2004 | Bardy |
| 6,719,701 | B2 | 4/2004 | Lade |
| 6,754,523 | B2 | 6/2004 | Toole |
| 6,782,293 | B2 | 8/2004 | Dupelle et al. |
| 6,856,832 | B1 | 2/2005 | Matsumura et al. |
| 6,860,897 | B2 | 3/2005 | Bardy |
| 6,866,629 | B2 | 3/2005 | Bardy |
| 6,887,201 | B2 | 5/2005 | Bardy |
| 6,893,397 | B2 | 5/2005 | Bardy |
| 6,895,261 | B1 | 5/2005 | Palamides |
| 6,904,312 | B2 | 6/2005 | Bardy |
| 6,908,431 | B2 | 6/2005 | Bardy |
| 6,913,577 | B2 | 7/2005 | Bardy |
| 6,944,498 | B2 | 9/2005 | Owen et al. |
| 6,960,167 | B2 | 11/2005 | Bardy |
| 6,970,731 | B1 | 11/2005 | Jayaraman et al. |
| 6,978,169 | B1 | 12/2005 | Guerra |
| 6,993,377 | B2 | 1/2006 | Flick et al. |
| 7,020,508 | B2 | 3/2006 | Stivoric et al. |
| 7,027,864 | B2 | 4/2006 | Snyder et al. |
| 7,052,472 | B1 | 5/2006 | Miller et al. |
| 7,065,401 | B2 | 6/2006 | Worden |
| 7,085,601 | B1 | 8/2006 | Bardy et al. |
| 7,104,955 | B2 | 9/2006 | Bardy |
| 7,134,996 | B2 | 11/2006 | Bardy |
| 7,137,389 | B2 | 11/2006 | Berthon-Jones |
| 7,147,600 | B2 | 12/2006 | Bardy |
| 7,153,265 | B2 | 12/2006 | Vachon |
| 7,187,985 | B2 | 3/2007 | Carim |
| 7,197,357 | B2 | 3/2007 | Istvan et al. |
| 7,206,630 | B1 | 4/2007 | Tarler |
| 7,212,849 | B2 | 5/2007 | Zhang et al. |
| 7,215,991 | B2 | 5/2007 | Besson et al. |
| 7,248,916 | B2 | 7/2007 | Bardy |
| 7,257,438 | B2 | 8/2007 | Kinast |
| 7,277,752 | B2 | 10/2007 | Matos |
| 7,294,108 | B1 | 11/2007 | Bornzin et al. |
| D558,882 | S | 1/2008 | Brady et al. |
| 7,328,061 | B2 | 2/2008 | Rowlandson |
| 7,382,247 | B2 | 6/2008 | Welch et al. |
| 7,395,106 | B2 | 7/2008 | Ryu et al. |
| 7,412,395 | B2 | 8/2008 | Rowlandson et al. |
| 7,429,938 | B1 | 9/2008 | Corndorf |
| 7,433,731 | B2 | 10/2008 | Matsumura et al. |
| 7,468,032 | B2 | 12/2008 | Stahmann et al. |
| 7,471,976 | B2 | 12/2008 | Lin et al. |
| 7,552,031 | B2 | 6/2009 | Vock et al. |
| 7,621,877 | B2 | 11/2009 | Schnall |
| D606,656 | S | 12/2009 | Kobayashi et al. |
| 7,664,552 | B2 | 2/2010 | Wahlstrand et al. |
| 7,672,714 | B2 | 3/2010 | Kuo et al. |
| 7,697,997 | B2 | 4/2010 | Hyatt et al. |
| 7,706,870 | B2 | 4/2010 | Shieh et al. |
| 7,756,721 | B1 | 7/2010 | Falchuk et al. |
| 7,761,143 | B2 | 7/2010 | Matsumura et al. |
| 7,787,943 | B2 | 8/2010 | McDonough |
| 7,874,993 | B2 | 1/2011 | Bardy |
| 7,881,785 | B2 | 2/2011 | Nassif et al. |
| D639,437 | S | 6/2011 | Bishay et al. |
| 7,959,574 | B2 | 6/2011 | Bardy |
| 7,970,450 | B2 | 6/2011 | Kroecker et al. |
| 8,016,776 | B2 | 9/2011 | Bourget et al. |
| 8,108,035 | B1 | 1/2012 | Bharmi |
| 8,116,841 | B2 | 2/2012 | Bly et al. |
| 8,135,459 | B2 | 3/2012 | Bardy et al. |
| 8,150,502 | B2 | 4/2012 | Kumar et al. |
| 8,160,682 | B2 | 4/2012 | Kumar et al. |
| 8,172,761 | B2 | 5/2012 | Rulkov et al. |
| 8,180,425 | B2 | 5/2012 | Selvitelli et al. |
| 8,200,320 | B2 | 6/2012 | Kovacs |
| 8,214,007 | B2 | 7/2012 | Baker et al. |
| 8,231,539 | B2 | 7/2012 | Bardy |
| 8,231,540 | B2 | 7/2012 | Bardy |
| 8,239,012 | B2 | 8/2012 | Felix et al. |
| 8,244,335 | B2 | 8/2012 | Kumar et al. |
| 8,249,686 | B2 | 8/2012 | Libbus et al. |
| 8,260,414 | B2 | 9/2012 | Nassif et al. |
| 8,260,439 | B2 | 9/2012 | DiUbaldi et al. |
| 8,266,008 | B1 | 9/2012 | Siegel et al. |
| 8,277,378 | B2 | 10/2012 | Bardy |
| 8,285,356 | B2 | 10/2012 | Bly et al. |
| 8,285,370 | B2 | 10/2012 | Felix et al. |
| 8,308,650 | B2 | 11/2012 | Bardy |
| 8,315,695 | B2 | 11/2012 | Sebelius et al. |
| 8,334,464 | B2 | 12/2012 | Edwards et al. |
| 8,366,629 | B2 | 2/2013 | Bardy |
| 8,374,688 | B2 | 2/2013 | Libbus et al. |
| 8,412,317 | B2 | 4/2013 | Mazar |
| 8,460,189 | B2 | 6/2013 | Libbus et al. |
| 8,473,047 | B2 | 6/2013 | Chakravarthy et al. |
| 8,478,418 | B2 | 7/2013 | Fahey |
| 8,483,809 | B2 | 7/2013 | Kim et al. |
| 8,538,503 | B2 | 9/2013 | Kumar et al. |
| 8,545,416 | B1 | 10/2013 | Kayyali et al. |
| 8,554,311 | B2 | 10/2013 | Warner et al. |
| 8,560,046 | B2 | 10/2013 | Kumar et al. |
| 8,591,430 | B2 | 11/2013 | Amurthur et al. |
| 8,594,763 | B1 | 11/2013 | Bibian et al. |
| 8,600,486 | B2 | 12/2013 | Kaib et al. |
| 8,611,980 | B2 | 12/2013 | Choe et al. |
| 8,613,708 | B2 | 12/2013 | Bishay et al. |
| 8,613,709 | B2 | 12/2013 | Bishay et al. |
| 8,615,282 | B2 | 12/2013 | Brister et al. |

(56) References Cited

U.S. PATENT DOCUMENTS

| | | | |
|---|---|---|---|
| 8,620,418 B1 | 12/2013 | Kuppuraj et al. | |
| 8,626,262 B2 | 1/2014 | McGusty et al. | |
| 8,626,277 B2 | 1/2014 | Felix et al. | |
| 8,628,020 B2 | 1/2014 | Beck | |
| 8,630,699 B2 | 1/2014 | Baker et al. | |
| 8,632,463 B2 | 1/2014 | Drinan et al. | |
| 8,647,268 B2 | 2/2014 | Tran | |
| 8,668,653 B2 | 3/2014 | Nagata et al. | |
| 8,684,925 B2 | 4/2014 | Manicka et al. | |
| 8,688,190 B2 | 4/2014 | Libbus et al. | |
| 8,718,736 B2 | 5/2014 | Gonopolskiy et al. | |
| 8,718,742 B2 | 5/2014 | Beck et al. | |
| 8,718,752 B2 | 5/2014 | Libbus et al. | |
| 8,744,561 B2 | 6/2014 | Fahey | |
| 8,750,974 B2 | 6/2014 | Baker et al. | |
| 8,774,932 B2 | 7/2014 | Fahey | |
| 8,790,257 B2 | 7/2014 | Libbus et al. | |
| 8,790,259 B2 | 7/2014 | Katra et al. | |
| 8,795,174 B2 | 8/2014 | Manicka et al. | |
| 8,798,729 B2 | 8/2014 | Kaib et al. | |
| 8,798,734 B2 | 8/2014 | Kuppuraj et al. | |
| 8,818,478 B2 | 8/2014 | Scheffler et al. | |
| 8,818,481 B2 | 8/2014 | Bly et al. | |
| 8,823,490 B2 | 9/2014 | Libbus et al. | |
| 8,858,432 B2 | 10/2014 | Robertson et al. | |
| 8,911,383 B2 | 12/2014 | Christensen et al. | |
| 8,926,509 B2 | 1/2015 | Magar et al. | |
| 8,938,287 B2 | 1/2015 | Felix et al. | |
| 8,948,935 B1 | 2/2015 | Peeters et al. | |
| 8,965,492 B2 | 2/2015 | Baker et al. | |
| 8,983,594 B2 | 3/2015 | Saar et al. | |
| 9,066,664 B2 | 6/2015 | Karjalainen | |
| 9,135,608 B2 | 9/2015 | Herlitz | |
| 9,149,229 B1 | 10/2015 | Tarler | |
| 9,155,484 B2 | 10/2015 | Baker et al. | |
| 9,173,670 B2 | 11/2015 | Sepulveda et al. | |
| 9,183,738 B1 | 11/2015 | Allen, Sr. et al. | |
| 9,204,813 B2 | 12/2015 | Kaib et al. | |
| 9,211,073 B2 | 12/2015 | Banet et al. | |
| 9,241,649 B2 | 1/2016 | Kumar et al. | |
| 9,259,154 B2 | 2/2016 | Miller et al. | |
| 9,267,793 B2 | 2/2016 | Vock et al. | |
| 9,277,864 B2 | 3/2016 | Yang et al. | |
| 9,277,871 B2 | 3/2016 | Keenan et al. | |
| 9,339,202 B2 | 5/2016 | Brockway et al. | |
| 9,375,179 B2 | 6/2016 | Schultz et al. | |
| 9,414,786 B1 | 8/2016 | Brockway et al. | |
| 9,433,366 B2 | 9/2016 | Baker et al. | |
| 9,439,566 B2 | 9/2016 | Arne et al. | |
| 9,451,975 B2 | 9/2016 | Sepulveda et al. | |
| 9,469,599 B2 | 10/2016 | Kanj et al. | |
| 9,510,755 B2 | 12/2016 | Fong et al. | |
| 9,603,542 B2 | 3/2017 | Veen et al. | |
| 9,669,212 B2 | 6/2017 | Mueller et al. | |
| 9,693,732 B1 | 7/2017 | Tarler | |
| 9,700,222 B2 | 7/2017 | Quinlan et al. | |
| 9,757,554 B2 | 9/2017 | Dar et al. | |
| 9,770,182 B2 | 9/2017 | Bly et al. | |
| 9,877,663 B2 | 1/2018 | Baker et al. | |
| 10,034,614 B2 | 7/2018 | Edic et al. | |
| 10,045,708 B2 | 8/2018 | Dusan | |
| 10,049,182 B2 | 8/2018 | Chefles et al. | |
| 10,159,422 B2 | 12/2018 | Baker et al. | |
| 10,244,949 B2 | 4/2019 | Moyer et al. | |
| 10,271,754 B2 | 4/2019 | Bahney et al. | |
| 10,327,660 B2 | 6/2019 | Gallego et al. | |
| 10,405,799 B2 | 9/2019 | Kumar et al. | |
| 10,413,251 B2 | 9/2019 | Golda et al. | |
| 10,441,185 B2 | 10/2019 | Rogers et al. | |
| 10,517,500 B2 | 12/2019 | Kumar et al. | |
| 10,555,683 B2 | 2/2020 | Bahney et al. | |
| 10,939,839 B2 | 3/2021 | Baker et al. | |
| 11,051,738 B2 | 7/2021 | Bahney et al. | |
| 11,051,743 B2 | 7/2021 | Felix et al. | |
| 11,116,447 B2 | 9/2021 | Yang et al. | |
| 11,141,091 B2 | 10/2021 | Kumar et al. | |
| 11,445,967 B2 | 9/2022 | Felix et al. | |
| 11,627,902 B2 | 4/2023 | Bahney et al. | |
| 12,133,734 B2 | 11/2024 | Kumar et al. | |
| 12,245,859 B2 | 3/2025 | Bahney et al. | |
| 12,245,860 B2 | 3/2025 | Bahney et al. | |
| 12,274,554 B2 | 4/2025 | Kumar et al. | |
| 12,285,261 B2 | 4/2025 | Bishay et al. | |
| 12,303,275 B2 | 5/2025 | Bahney et al. | |
| 12,303,277 B2 | 5/2025 | Kumar et al. | |
| 2001/0051766 A1 | 12/2001 | Gazdzinski | |
| 2002/0013538 A1 | 1/2002 | Teller | |
| 2002/0013717 A1 | 1/2002 | Ando et al. | |
| 2002/0016798 A1 | 2/2002 | Sakai et al. | |
| 2002/0072682 A1 | 6/2002 | Hopman et al. | |
| 2002/0082491 A1 | 6/2002 | Nissila | |
| 2002/0082867 A1 | 6/2002 | MacCarter et al. | |
| 2002/0099277 A1 | 7/2002 | Harry et al. | |
| 2002/0103422 A1 | 8/2002 | Harder et al. | |
| 2002/0106709 A1 | 8/2002 | Potts et al. | |
| 2002/0107436 A1 | 8/2002 | Barton et al. | |
| 2002/0109621 A1 | 8/2002 | Khair et al. | |
| 2002/0120310 A1 | 8/2002 | Linden et al. | |
| 2002/0128686 A1 | 9/2002 | Minogue et al. | |
| 2002/0184055 A1 | 12/2002 | Naghavi et al. | |
| 2002/0193668 A1 | 12/2002 | Munneke et al. | |
| 2003/0004547 A1 | 1/2003 | Owen et al. | |
| 2003/0028811 A1 | 2/2003 | Walker et al. | |
| 2003/0055460 A1 | 3/2003 | Owen et al. | |
| 2003/0069510 A1 | 4/2003 | Semler et al. | |
| 2003/0073916 A1 | 4/2003 | Yonce | |
| 2003/0083559 A1 | 5/2003 | Thompson | |
| 2003/0097078 A1 | 5/2003 | Maeda | |
| 2003/0139785 A1 | 7/2003 | Riff et al. | |
| 2003/0149349 A1 | 8/2003 | Jensen | |
| 2003/0149439 A1 | 8/2003 | Wendlandt | |
| 2003/0174881 A1 | 9/2003 | Simard et al. | |
| 2003/0176802 A1 | 9/2003 | Galen et al. | |
| 2003/0211797 A1 | 11/2003 | Hill et al. | |
| 2003/0216662 A1 | 11/2003 | Jersey-Willuhn et al. | |
| 2004/0008123 A1 | 1/2004 | Carrender et al. | |
| 2004/0019288 A1 | 1/2004 | Kinast | |
| 2004/0034284 A1 | 2/2004 | Aversano et al. | |
| 2004/0049120 A1 | 3/2004 | Cao et al. | |
| 2004/0049132 A1 | 3/2004 | Barron et al. | |
| 2004/0073127 A1 | 4/2004 | Istvan et al. | |
| 2004/0087836 A1 | 5/2004 | Green et al. | |
| 2004/0088019 A1 | 5/2004 | Rueter et al. | |
| 2004/0093192 A1 | 5/2004 | Hasson et al. | |
| 2004/0116784 A1 | 6/2004 | Gavish | |
| 2004/0148194 A1 | 7/2004 | Wellons et al. | |
| 2004/0163034 A1 | 8/2004 | Colbath et al. | |
| 2004/0167416 A1 | 8/2004 | Lee | |
| 2004/0171921 A1 | 9/2004 | Say et al. | |
| 2004/0207530 A1 | 10/2004 | Nielsen | |
| 2004/0210165 A1 | 10/2004 | Marmaropoulos et al. | |
| 2004/0220486 A1 | 11/2004 | Baumer et al. | |
| 2004/0236202 A1 | 11/2004 | Burton | |
| 2004/0243435 A1 | 12/2004 | Williams | |
| 2004/0256453 A1 | 12/2004 | Lammle | |
| 2004/0260188 A1 | 12/2004 | Syed et al. | |
| 2004/0260192 A1 | 12/2004 | Yamamoto | |
| 2005/0010139 A1 | 1/2005 | Aminian et al. | |
| 2005/0043640 A1 | 2/2005 | Chang | |
| 2005/0058701 A1 | 3/2005 | Gross et al. | |
| 2005/0096513 A1 | 5/2005 | Ozguz et al. | |
| 2005/0096717 A1 | 5/2005 | Bishay et al. | |
| 2005/0101875 A1 | 5/2005 | Semler et al. | |
| 2005/0108055 A1 | 5/2005 | Ott et al. | |
| 2005/0113661 A1 | 5/2005 | Nazeri et al. | |
| 2005/0137485 A1 | 6/2005 | Cao et al. | |
| 2005/0151640 A1 | 7/2005 | Hastings | |
| 2005/0154267 A1 | 7/2005 | Bardy | |
| 2005/0154294 A1 | 7/2005 | Uchiyama et al. | |
| 2005/0182308 A1 | 8/2005 | Bardy | |
| 2005/0182309 A1 | 8/2005 | Bardy | |
| 2005/0215918 A1 | 9/2005 | Frantz et al. | |
| 2005/0222513 A1 | 10/2005 | Hadley et al. | |
| 2005/0228243 A1 | 10/2005 | Bardy | |

(56)        References Cited

U.S. PATENT DOCUMENTS

| | | |
|---|---|---|
| 2005/0245797 A1 | 11/2005 | Al-Ali et al. |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0020217 A1 | 1/2006 | Lin |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030781 A1 | 2/2006 | Shennib |
| 2006/0030904 A1 | 2/2006 | Quiles |
| 2006/0041201 A1 | 2/2006 | Behbehani et al. |
| 2006/0052999 A1 | 3/2006 | Brooks et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0111943 A1 | 5/2006 | Wu |
| 2006/0122469 A1 | 6/2006 | Martel |
| 2006/0124193 A1 | 6/2006 | Orr et al. |
| 2006/0167502 A1 | 7/2006 | Haefner |
| 2006/0224072 A1 | 10/2006 | Shennib |
| 2006/0229522 A1 | 10/2006 | Barr |
| 2006/0235316 A1 | 10/2006 | Ungless et al. |
| 2006/0235320 A1 | 10/2006 | Tan et al. |
| 2006/0238333 A1 | 10/2006 | Welch et al. |
| 2006/0247509 A1 | 11/2006 | Tuccillo et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2006/0282001 A1 | 12/2006 | Noel et al. |
| 2007/0003115 A1 | 1/2007 | Patton et al. |
| 2007/0029961 A1 | 2/2007 | Harita et al. |
| 2007/0038057 A1 | 2/2007 | Nam et al. |
| 2007/0050209 A1 | 3/2007 | Yered |
| 2007/0060862 A1 | 3/2007 | Sun et al. |
| 2007/0069887 A1 | 3/2007 | Welch et al. |
| 2007/0073132 A1 | 3/2007 | Vosch |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0088419 A1 | 4/2007 | Fiorina et al. |
| 2007/0088429 A1 | 4/2007 | Thompson |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100666 A1 | 5/2007 | Stivoric et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0142722 A1 | 6/2007 | Chang |
| 2007/0173892 A1 | 7/2007 | Fleischer et al. |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0206655 A1 | 9/2007 | Haslett et al. |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0233198 A1 | 10/2007 | Ghanem et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem et al. |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293742 A1 | 12/2007 | Bardy |
| 2007/0293781 A1 | 12/2007 | Sims et al. |
| 2007/0299325 A1 | 12/2007 | Farrell et al. |
| 2007/0299617 A1 | 12/2007 | Willis |
| 2008/0027337 A1 | 1/2008 | Dugan |
| 2008/0027339 A1 | 1/2008 | Nagai et al. |
| 2008/0051668 A1 | 2/2008 | Bardy |
| 2008/0058661 A1 | 3/2008 | Bardy |
| 2008/0088467 A1 | 4/2008 | Al-Ali et al. |
| 2008/0091089 A1 | 4/2008 | Guillory et al. |
| 2008/0091090 A1 | 4/2008 | Guillory et al. |
| 2008/0091097 A1 | 4/2008 | Linti et al. |
| 2008/0108889 A1 | 5/2008 | Lin et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0171918 A1 | 7/2008 | Teller et al. |
| 2008/0177168 A1 | 7/2008 | Callahan et al. |
| 2008/0182204 A1 | 7/2008 | Calvert et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0214949 A1 | 9/2008 | Stivoric et al. |
| 2008/0214985 A1 | 9/2008 | Yanaki |
| 2008/0243012 A1 | 10/2008 | Hisayuki et al. |
| 2008/0269657 A1 | 10/2008 | Brenneman et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0306397 A1 | 12/2008 | Bonmassar et al. |
| 2008/0309481 A1 | 12/2008 | Tanaka et al. |
| 2008/0312522 A1 | 12/2008 | Rowlandson et al. |
| 2008/0312524 A1 | 12/2008 | Solosko et al. |
| 2009/0009342 A1 | 1/2009 | Karjalainen |
| 2009/0012412 A1 | 1/2009 | Wiesel |
| 2009/0012979 A1 | 1/2009 | Bateni et al. |
| 2009/0048563 A1 | 2/2009 | Ethelfeld et al. |
| 2009/0054737 A1 | 2/2009 | Magar et al. |
| 2009/0054952 A1 | 2/2009 | Glukhovsky et al. |
| 2009/0062670 A1 | 3/2009 | Sterling et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0093687 A1 | 4/2009 | Telfort et al. |
| 2009/0099469 A1 | 4/2009 | Flores |
| 2009/0105632 A1 | 4/2009 | Padmanabhan et al. |
| 2009/0112116 A1 | 4/2009 | Lee et al. |
| 2009/0131759 A1 | 5/2009 | Sims et al. |
| 2009/0133047 A1 | 5/2009 | Lee et al. |
| 2009/0156908 A1 | 6/2009 | Belalcazar et al. |
| 2009/0171258 A1 | 7/2009 | Stroebeck et al. |
| 2009/0177068 A1 | 7/2009 | Stivoric et al. |
| 2009/0177073 A1 | 7/2009 | Sonnenborg |
| 2009/0182204 A1 | 7/2009 | Semler et al. |
| 2009/0216132 A1 | 8/2009 | Orbach |
| 2009/0264792 A1 | 10/2009 | Mazar |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2009/0327715 A1 | 12/2009 | Smith et al. |
| 2010/0007413 A1 | 1/2010 | Herleikson |
| 2010/0016701 A1 | 1/2010 | Cheng et al. |
| 2010/0022897 A1 | 1/2010 | Parker et al. |
| 2010/0056877 A1 | 3/2010 | Fein et al. |
| 2010/0056881 A1 | 3/2010 | Libbus et al. |
| 2010/0056972 A1 | 3/2010 | Harima et al. |
| 2010/0063365 A1 | 3/2010 | Pisani et al. |

(56) References Cited

U.S. PATENT DOCUMENTS

| | | |
|---|---|---|
| 2010/0076517 A1 | 3/2010 | Imran |
| 2010/0081913 A1 | 4/2010 | Cross et al. |
| 2010/0137694 A1 | 6/2010 | Irazoqui et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234697 A1 | 9/2010 | Walter et al. |
| 2010/0234700 A1 | 9/2010 | Bowers |
| 2010/0234715 A1 | 9/2010 | Shin et al. |
| 2010/0234716 A1 | 9/2010 | Engel |
| 2010/0268103 A1 | 10/2010 | McNamara et al. |
| 2010/0280366 A1 | 11/2010 | Arne et al. |
| 2010/0298720 A1 | 11/2010 | Potkay |
| 2010/0305416 A1 | 12/2010 | Bédard et al. |
| 2010/0312188 A1 | 12/2010 | Robertson et al. |
| 2010/0317957 A1 | 12/2010 | Lee et al. |
| 2010/0324384 A1 | 12/2010 | Moon et al. |
| 2010/0324405 A1 | 12/2010 | Niemi et al. |
| 2011/0006902 A1 | 1/2011 | Saigh |
| 2011/0009729 A1 | 1/2011 | Shin et al. |
| 2011/0021937 A1 | 1/2011 | Hugh et al. |
| 2011/0054285 A1 | 3/2011 | Searle et al. |
| 2011/0054286 A1 | 3/2011 | Crosby |
| 2011/0060215 A1 | 3/2011 | Tupin, Jr. et al. |
| 2011/0066041 A1 | 3/2011 | Pandia et al. |
| 2011/0077497 A1 | 3/2011 | Oster et al. |
| 2011/0082842 A1 | 4/2011 | Groseclose, Jr. et al. |
| 2011/0098549 A1 | 4/2011 | Bar Hayim et al. |
| 2011/0105861 A1 | 5/2011 | Derchak et al. |
| 2011/0112379 A1 | 5/2011 | Li et al. |
| 2011/0125040 A1 | 5/2011 | Crawford et al. |
| 2011/0144470 A1 | 6/2011 | Mazar et al. |
| 2011/0160548 A1 | 6/2011 | Forster |
| 2011/0160601 A1 | 6/2011 | Wang et al. |
| 2011/0166529 A1 | 7/2011 | LeLievre et al. |
| 2011/0208076 A1 | 8/2011 | Fong et al. |
| 2011/0224564 A1 | 9/2011 | Moon et al. |
| 2011/0230739 A1 | 9/2011 | Gretz et al. |
| 2011/0237922 A1 | 9/2011 | Parker, III et al. |
| 2011/0237924 A1 | 9/2011 | McGusty et al. |
| 2011/0245648 A1 | 10/2011 | Hudson |
| 2011/0245699 A1 | 10/2011 | Snell et al. |
| 2011/0245711 A1 | 10/2011 | Katra et al. |
| 2011/0279963 A1 | 11/2011 | Kumar et al. |
| 2011/0288605 A1 | 11/2011 | Kaib et al. |
| 2011/0301490 A1 | 12/2011 | Mucke et al. |
| 2011/0313305 A1 | 12/2011 | Rantala |
| 2012/0003933 A1 | 1/2012 | Baker et al. |
| 2012/0029300 A1 | 2/2012 | Paquet |
| 2012/0029306 A1 | 2/2012 | Paquet et al. |
| 2012/0029307 A1 | 2/2012 | Paquet et al. |
| 2012/0029309 A1 | 2/2012 | Paquet et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | Mcdonald et al. |
| 2012/0079127 A1 | 3/2012 | Hadland |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0108917 A1 | 5/2012 | Libbus et al. |
| 2012/0108993 A1 | 5/2012 | Gordon et al. |
| 2012/0158075 A1 | 6/2012 | Kaib et al. |
| 2012/0165645 A1 | 6/2012 | Russell et al. |
| 2012/0172695 A1 | 7/2012 | Ko et al. |
| 2012/0179665 A1 | 7/2012 | Baarman et al. |
| 2012/0184207 A1 | 7/2012 | Gaines |
| 2012/0197118 A1 | 8/2012 | Lisiecki et al. |
| 2012/0215123 A1 | 8/2012 | Kumar et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0265080 A1 | 10/2012 | Yu et al. |
| 2012/0265738 A1 | 10/2012 | Beckmann et al. |
| 2012/0302906 A1 | 11/2012 | Felix et al. |
| 2012/0306662 A1 | 12/2012 | Vosch et al. |
| 2012/0323098 A1 | 12/2012 | Moein et al. |
| 2012/0323132 A1 | 12/2012 | Warner et al. |
| 2012/0330126 A1 | 12/2012 | Hoppe et al. |
| 2013/0041272 A1 | 2/2013 | Guillén Arredondo et al. |
| 2013/0077263 A1 | 3/2013 | Oleson et al. |
| 2013/0079611 A1 | 3/2013 | Besko |
| 2013/0079618 A1 | 3/2013 | Sandmore et al. |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0109937 A1 | 5/2013 | Banet et al. |
| 2013/0116533 A1 | 5/2013 | Lian et al. |
| 2013/0123651 A1 | 5/2013 | Bardy |
| 2013/0124891 A1 | 5/2013 | Donaldson |
| 2013/0131530 A1 | 5/2013 | Brockway et al. |
| 2013/0158361 A1 | 6/2013 | Bardy |
| 2013/0172763 A1 | 7/2013 | Wheeler |
| 2013/0197341 A1 | 8/2013 | Grob et al. |
| 2013/0197380 A1 | 8/2013 | Oral et al. |
| 2013/0225963 A1 | 8/2013 | Kodandaramaiah et al. |
| 2013/0225966 A1 | 8/2013 | Macia Barber et al. |
| 2013/0225967 A1 | 8/2013 | Esposito |
| 2013/0226018 A1 | 8/2013 | Kumar et al. |
| 2013/0231947 A1 | 9/2013 | Shusterman |
| 2013/0243105 A1 | 9/2013 | Lei et al. |
| 2013/0274565 A1 | 10/2013 | Langer et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325096 A1 | 12/2013 | Dupelle et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0002234 A1 | 1/2014 | Alwan |
| 2014/0005502 A1 | 1/2014 | Klap et al. |
| 2014/0012154 A1 | 1/2014 | Mazar et al. |
| 2014/0031663 A1 | 1/2014 | Gallego |
| 2014/0056452 A1 | 2/2014 | Moss et al. |
| 2014/0088399 A1 | 3/2014 | Lian et al. |
| 2014/0094676 A1 | 4/2014 | Gani et al. |
| 2014/0107509 A1 | 4/2014 | Banet et al. |
| 2014/0121557 A1 | 5/2014 | Gannon et al. |
| 2014/0140359 A1 | 5/2014 | Kalevo et al. |
| 2014/0142411 A1 | 5/2014 | Lin et al. |
| 2014/0148718 A1 | 5/2014 | Stickney et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0213937 A1 | 7/2014 | Bianchi et al. |
| 2014/0214134 A1 | 7/2014 | Peterson |
| 2014/0215246 A1 | 7/2014 | Lee et al. |
| 2014/0228656 A1 | 8/2014 | Gonopolskiy et al. |
| 2014/0249852 A1 | 9/2014 | Proud |
| 2014/0280027 A1 | 9/2014 | Cordes et al. |
| 2014/0296651 A1 | 10/2014 | Stone |
| 2014/0297310 A1 | 10/2014 | Collins, Jr. |
| 2014/0318699 A1 | 10/2014 | Longinotti-Buitoni et al. |
| 2014/0330147 A1 | 11/2014 | Ousdigian et al. |

(56) References Cited

U.S. PATENT DOCUMENTS

| | | |
|---|---|---|
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0018660 A1 | 1/2015 | Thomson et al. |
| 2015/0022372 A1 | 1/2015 | Vosch |
| 2015/0048836 A1 | 2/2015 | Guthrie et al. |
| 2015/0065842 A1 | 3/2015 | Lee et al. |
| 2015/0087950 A1 | 3/2015 | Felix et al. |
| 2015/0094558 A1 | 4/2015 | Russell |
| 2015/0142090 A1 | 5/2015 | Duijsens et al. |
| 2015/0177175 A1 | 6/2015 | Elder et al. |
| 2015/0202351 A1 | 7/2015 | Kaplan et al. |
| 2015/0250422 A1* | 9/2015 | Bay ................... A61B 5/0533 |
| | | 600/391 |
| 2015/0257670 A1 | 9/2015 | Ortega et al. |
| 2015/0305676 A1 | 10/2015 | Shoshani |
| 2015/0335285 A1 | 11/2015 | Poon et al. |
| 2015/0342526 A1 | 12/2015 | Totman et al. |
| 2015/0359489 A1 | 12/2015 | Baudenbacher et al. |
| 2016/0029917 A1 | 2/2016 | Baker et al. |
| 2016/0135746 A1 | 5/2016 | Kumar et al. |
| 2016/0217691 A1 | 7/2016 | Kadobayashi et al. |
| 2018/0020931 A1 | 1/2018 | Shusterman |
| 2019/0021671 A1 | 1/2019 | Kumar et al. |
| 2019/0117068 A1 | 4/2019 | Thomson et al. |
| 2019/0223806 A1 | 7/2019 | Bennet et al. |
| 2020/0121209 A1 | 4/2020 | Kumar et al. |
| 2021/0315504 A1 | 10/2021 | Kumar et al. |
| 2023/0248288 A1 | 8/2023 | Bahney et al. |
| 2024/0398310 A1 | 12/2024 | Kumar et al. |

FOREIGN PATENT DOCUMENTS

| | | |
|---|---|---|
| CN | 101163440 A | 4/2008 |
| DE | 19611414 A1 | 9/1997 |
| DE | 29805334 U1 | 7/1998 |
| DE | 19955211 | 5/2001 |
| DE | 10347303 A1 | 5/2005 |
| DE | 102004007712 A1 | 10/2005 |
| EP | 1090583 A1 | 4/2001 |
| EP | 1782730 A1 | 5/2007 |
| EP | 1859833 | 11/2007 |
| EP | 2081488 A2 | 7/2009 |
| EP | 1979040 B1 | 9/2009 |
| EP | 2438851 | 4/2012 |
| EP | 2438852 | 4/2012 |
| EP | 2465415 | 6/2012 |
| EP | 2589333 | 5/2013 |
| GB | 2350193 B | 4/2003 |
| JP | H06319711 | 11/1994 |
| JP | H11188015 | 7/1999 |
| JP | H11212159 A | 8/1999 |
| JP | 2002181641 A | 6/2002 |
| JP | 2004121360 | 4/2004 |
| JP | 2004129788 | 4/2004 |
| JP | 2005340087 A | 12/2005 |
| JP | 2007082938 | 4/2007 |
| JP | 2009219554 | 10/2009 |
| JP | 2012033508 A | 2/2012 |
| JP | 2012220849 A | 11/2012 |
| KR | 20120087633 A | 8/2012 |
| KR | 20120112879 A | 10/2012 |
| WO | 8701024 | 2/1987 |
| WO | 9632058 A1 | 10/1996 |
| WO | 9843537 A1 | 10/1998 |
| WO | 9852463 | 11/1998 |
| WO | 9913765 A1 | 3/1999 |
| WO | 9959465 A1 | 11/1999 |
| WO | 0078213 | 12/2000 |
| WO | 2002022006 | 3/2002 |
| WO | 0332192 | 4/2003 |
| WO | 0365926 | 8/2003 |
| WO | 2005084533 | 9/2005 |
| WO | 2006009767 | 1/2006 |
| WO | 2006014806 | 2/2006 |
| WO | 2006109072 | 10/2006 |
| WO | 2007066270 | 6/2007 |
| WO | 2007081745 A2 | 7/2007 |
| WO | 2007092543 | 8/2007 |
| WO | 2008005015 | 1/2008 |
| WO | 2008005016 | 1/2008 |
| WO | 2008006150 A1 | 1/2008 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009050702 A2 | 4/2009 |
| WO | 2009083980 A2 | 7/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010104952 | 9/2010 |
| WO | 2010105045 | 9/2010 |
| WO | 2010107913 A2 | 9/2010 |
| WO | 2011047207 | 4/2011 |
| WO | 2012040487 | 3/2012 |
| WO | 2012104657 | 8/2012 |
| WO | 2012112407 | 8/2012 |
| WO | 2012125424 A2 | 9/2012 |
| WO | 2012125425 A2 | 9/2012 |
| WO | 2012140559 | 10/2012 |
| WO | 2012146957 | 11/2012 |
| WO | 2012149466 A2 | 11/2012 |

OTHER PUBLICATIONS

Complaint from Case No. 1 :22-cv-00351-UNA, *Bardy Diagnostics, Inc.* (Plaintiff) v . *Vital Connect, Inc.* (Defendant), filed: Mar. 18, 2022, 182 pages.

Corventis Avivo, "Aviva Mobile Patient Management System", Corventis, 2008, lasted printed Jul. 18, 2024, https://web. archive.org/web/20100118155329/http://www.corventis.com/AP/avivo.Asp.

Corventis Nuvant, "Nuvant Mobile Cardiac Telementry (MTC) System", Corventis, 2009, last printed Jul. 18, 2024, https://web.archive.org/web/20100127193736/http://corventis. com/AP/nuvant. Asp.

Daoud et al. "Fall Detection Using Shimmer Technology And Multiresolution Analysis." Aug. 2, 2013. URL: https://decibel.ni.com/content/docs/DOC-26652.

Dec. 26, 2022 Letter from Opposing Counsel, 1:22-cv-00351-CJB; *Bardy Diagnostics, Inc.* v_ *Vital Connect, Inc.* D. Del.); and IPR2023-00381; *Vital Connect, Inc.* v. *Bardy Diagnostics, Inc.* (P.T.A.B.), Dec. 26, 2022.

Defendant's Answer, Defenses, and Counterclaim from Case. No. 1:22-cv-00351-CFC, *Bardy Diagnostics, Inc.* (Plaintiff) v. *Vital Connect, Inc.* (Defendant), Filed May 25, 2022, 132 pages.

Defendant's Opening Brief In Support of Its Motion To Dismiss For Failure to State A Claim from Case No. 1:22-v.00351-CFC, *Bardy Diagnostics, Inc.* (Plaintiff) v. *Vital Connect, Inc.* (Defendant), Filed: May 25, 2022, 18 pages.

Defendant's Reply Brief In Support of Its Motion to Dismiss For Failure to State a Claim from Case No. 1 :22-cv-00351- CFC, *Bardy Diagnostics, Inc.* (Plaintiff) v. *Vital Connect, Inc.* (Defendant), Filed: Jun. 15, 2022, 93 pages.

Duttweiler et al., "Probability Estimation In Arithmetic And Adaptive-Huffman Entropy Coders," IEEE Transactions in Image Processing_ vol. 4, No. 3, Mar. 1, 1995, pp. 237-246.

Epstein, Andrew E et al.; ACC/AHA/HRS 2008 Guidelines for Device-Based Therapy of Cardiac Rhythm Abnormalities. J. Am. Coll. Cardiol. 2008; 51; el-e62, 66 Pgs.

First Amended Complaint for Patent Infringement, 1:22-cv-00351-CJB, *Bardy Diagnostics, Inc_* v. *Vital Connect, Inc.* D. Del.), filed Jan. 10, 2023.

First Examination Report, Communication pursuant to Article 94(3) EPC, 19 828 053.9-1113, dated Apr. 15, 2024.

(56)            References Cited

OTHER PUBLICATIONS

Fitbit Tracker, URL <http://www.fitbit.com/> (Web page cached on Sep. 10, 2008.).

Gravitz, Lauren, "When Your Diet Needs A Band-Aid," Technology Review, MIT. (May 1, 2009).

Gupta et al., "An ECG Compression Technique For Telecardiology Application," India Conference (INDICON), 2011 Annual IEEE, Dec. 16, 2011, pp. 1-4.

Harland et al., "Electric Potential Probes-New Directions in the Remote Sensing of the Human Body", Measurement Science and Technology (2002), vol. 13, pp. 163-169.

Hill, "Adventures in Self-Surveillance: Fitbit, Tracking My Movement and Sleep," Forbes, Feb. 25, 2011, 11 pages.

http://www.gtec.at/Products/Software/g. BSanalyze-Specs-Features (2014 ).

http://www.originlab.com/origin#Data_Exploration 2015.

https://fccid.io/LF524950/User-Manual/User-Manual-1944573 © Medtronic, Inc. 2012.

https://web.archive.org/web/20130831204020/http://www .biopac. com/research .asp?Catl 0=37 &Main=Software (Aug. 2013).

Initial hands-on with sirdv activity tracker, URL <http://www. dcrainmaker.com/2013/09/polar-loop-firstlook.html> Sep. 17, 2013).

International Preliminary Report on Patentability and Written Opinion, PCT/US2019/064331, Jun. 8, 2021.

Invalidity of U.S. Pat. No. 11,051,743 by U.S. Pat. Pub. No. 2011/0077497 ("Oster"); Oct. 25, 2023; 11 pages.

IRhythm Zio XT Patch/Event Card, "Zio Patch", iRhythm, 2011, last printed Jul. 18, 2024, https://web.archive.org/web/2011101707 4139/http://irhythmtech.com/media/files/Z1 00A4020.04%20-%20ZIO%20PATCH%20DATA%20SHEET.pdf.

*IRhythm, Inc.* v. *Welch Allyn, Inc.*, Expert Declaration of Jason Heikenfeld for U.S. Patent Nos. 8,214,007, 8,965,492, 9,155,484, and 10,159,422 dated Dec. 20, 2024. 516 pages.

*IRhythm, Inc.* v. *Welch Allyn, Inc.*, Petition for Inter Partes Review Under 35 U.S.C. § 312 and 37 C.F.R. § 42.104, Case No. IPR2025-00363 for U.S. Pat. No. 10,159,422, dated Dec. 23, 2024. 94 pages.

*IRhythm, Inc.* v. *Welch Allyn, Inc.*, Petition for Inter Partes Review Under 35 U.S.C. § 312 and 37 C.F.R. § 42.104, Case No. IPR2025-00374 for U.S. Pat. No. 8,965,492, dated Dec. 23, 2024. 86 pages.

*IRhythm, Inc.* v. *Welch Allyn, Inc.*, Petition for Inter Partes Review Under 35 U.S.C. § 312 and 37 C.F.R. § 42.104, Case No. IPR2025-00376 for U.S. Pat. No. 9, 155,484, dated Dec. 23, 2024. 106 pages.

*IRhythm, Inc.* v. *Welch Allyn, Inc.*, Petition for Inter Partes Review Under 35 U.S.C. § 312 and 37 C.F.R. § 42.104, Case No. IPR2025-00377 for U.S. Pat. No. 8,214,007, dated Dec. 23, 2024. 88 pages.

*IRhythm, Inc.* v. *Welch Allyn, Inc.*, Petition for Inter Partes Review Under 35 U.S.C. § 312 and 37 C.F.R. § 42.104, Case No. IPR2025-00378 for U.S. Pat. No. 8,214,007, dated Dec. 23, 2024. 95 pages.

Ivanov, G.G., "HRV Analysis Under The Usage Of Different Electrocardiopraphy Systems," Apr. 15, 2008, (Apr. 15, 2008), XP55511209, Retrieved from the Internet: URL:http://www.drkucera. eu/upload_doc/hrv_analysis_methodical_recommendations)_pdf [retrieved on Oct. 1, 2018].

Kligfield, Paul et al., Recommendations for the Standardization and Interpretation of the Electrocardiogram: Part I. U. Am.Coll. Cardiol; 2007; 49; 1109-27, 75 Pgs.

Knight et al., U.S. Appl. No. 60/786,502, filed Mar. 29, 2006, 8 pages.

Leonard, Dwayne C., "A Framework for the Creation of a Unified Electronic Medical Record Using Biometrics", Data Fusion and Belief Theory (2007), <https://dialong.proquest.com/professional/docview/304852676/17AEEF1F9382EF1C4E5/6?accountid=131444> (last visited Aug. 27, 2021).

Libbus, "Adherent Cardiac Monitor With Wireless Fall Detection For Patients With Unexplained Syncope." Abstracts t>f the First AMA-IEEE Medical Technology Conference On Individualized Healthcare. May 22, 2010.

Lieberman, Jonathan "How Telemedicine Is Aiding Prompt ECG Diagnosis In Primary Care," British Journal of Community Nursing, vol. 13, No. 3, Mar. 1, 2008, pp. 123-126, XP009155082, ISSN: 1462-4753.

May 2, 2022 Letter From Counsel. 1:22-cv-00351-CFC. May 2, 2022.

May 24, 2022 Letter to Opposing Counsel. 1:22-cv-00351-CFC. May 24, 2022.

McManus et al., "A Novel Application for the Detection of an Irregular Pulse using an iphone 4S in Patients with Atrial Fibrillation," vol. 10(3), pp. 315-319 (Mar. 2013.).

Mehen, "Open health with the quantified self," Opensource.com, Aug. 25, 2011, 7 pages.

Mukala et al., "A Novel Zigbee-based Low-cost, Low-Power Wireless EKG system," IEEE, May 2010; 4 pages.

Nave et al., "ECG Compression Using Long-Term Prediction," IEEE Transactions on Biomedical Engineering, IEEE Service Center, Ny, USA, vol. 40, No. 9, Sep. 1, 1993, pp. 877-885.

Nike+ Fuel Band, URL <http://www.nike.com/us/en_us/c/nikeplus-fuelband> (Web page cached on Jan. 11, 2013.).

Nov. 11, 2022, Letter from Opposing Counsel, 1 :22-cv-00351-CJB; *Bardy Diagnostics, Inc.* v_ *Vital Connect, Inc. D.Del.*), Nov. 11, 2022.

Oct. 17, 2022 Letter to Opposing Counsel, *Bardy Diagnostics, Inc_* v_ *Vital Connect, Inc.*, No. 22-cv-00351-CFC D. Del.), Oct. 17, 2022.

P. Libby et al., "Braunwald's Heart Disease -A Textbook of Cardiovascular Medicine," Chs_ 11, pp. 125-148 and 12, pp. 149-193 (8th ed_ 2008), American Heart Association.

Pandian et al., "Wireless Sensor Network for Wearable Physiological Monitoring," Journal of Networks, vol. 3, No. 5, May 2008; 15 pages.

Petition for Inter Partes Review of U.S. Pat. No. 11,051,743 Pursuant To 35 U.S.C. §§ 311-319 and 37 C.F.R. § 42, Case No. IPR2023-00381, *Vital Connect, Inc.* v. *Bardy Diagnostics, Inc.* (P.T.A.B.), Dec. 21, 2022, 875 pages.

Plaintiff's Answer Brief in Opposition to Defendant's Motion to Dismiss For Failure to State a Claim from Case No. 1:22-cv-00351-CFC, *Bardy Diagnostics, Inc.* (Plaintiff) v. *Vital Connect, Inc.* (Defendant), Filed Jun. 8, 2022, 25 pages.

"23 Personal Tools to Learn More About Yourself," Flowingdata. com, Sep. 18, 2008, 18 pages.

15 Of The Hottest Wearable Gadgets, URL <http:/lthehottestgadgets. com/2008/09/the-15-hottest-wearable-gadgets-001253> (Web page cached on Sep. 27, 2008).

Actigraphy/ Circadian Rhythm SOMNOwatch, URL <http://www. somnomedics.eu/news-events publications/· omnowatchtm_html> (Web page cached on Jan. 23, 2010).

Adams et al., U.S. Appl. No. 61/755,623, filed Jan. 23, 2013, 48 pages.

Adinstruments: ECG Analysis Module For LabChart & Powerlab, 2008.

Alivecor, URL <http://www.businesswire.com/news/home/20121203005545/en/AliveCor%E2%80%99s-Heart-Monitor-Phone-Receives-FDA-Clearance#. U7rtq7FVTyF> (Dec. 3, 2012).

Alzaidi et al., "Smart Textiles Based Wireless ECG System," May 2012; 5 pages.

Anand et al., "Design of the Multi-Sensor Monitoring in Congestive Heart Failure (Music) Study: Prospective Trial to Assess the Utility of Continuous Wireless Physiologic Monitoring in Heart Failure", Journal of Cardiac Failure (2011), 17(1), pp. 11-16.

Anonymous Omegawave Launches Consumer App 2.0 in U.S. "Endurance Sportswire—Endurance Sportswire." Jul. 11, 2013. URL:http://endurancesportswire_com/omegawave-launches-consumer-app-2-0-in-u-s/.

Au-Yeung et al., U.S. Appl. No. 60/765,467, filed Feb. 6, 2006, 25 pages.

Aventyn, Inc., "Vital Connect, Aventyn Launch Wearable Biosensor Platform for Mobile Patient Monitoring", Dec. 12, 2013, 5 pages.

*Bardy Diagnostics, Inc.* v. *Vital Connect, Inc.*, Defendant's Identification of Supplemental Prior Art References, C.A. No. 22-351 (CJV), May 22, 2024.

(56) References Cited

OTHER PUBLICATIONS

*Bardy Diagnostics, Inc.*, Plaintiff v. *Vital Connect, Inc.*; The United States District Court for the District of Delaware; C.A. No. 22-351 (CJB); Vitalconnect's Preliminary Invalidity Contentions; filed Oct. 25, 2023.

Bharadwaj et al., Techniques for Accurate ECG signal processing, EE Times, URL <www.eetimes.com/document.asp?doc_id=1278571> (Feb. 14, 2011 ).

BIOPAC Systems, Inc. #AS148-Automated ECG Analysis, Mar. 24, 2006.

Cesario et al., "Arrhythmia Detection with a Low-Profile Wireless Adherent Cardiac Monitor: Results from the Adam and Eve Studies", The Journal of Innovations in Cardiac Rhythm Management (2011), pp. 476-482.

Chaimanonart et al., "A Wireless Batteryless in vivo EKG and Body Temperature Sensing Microsystem with Adaptive RF Powering for Genetically Engineered Mice Monitoring," Jul. 2009; 4 pages.

Chan et al., "Wireless Patch Sensor for Remote Monitoring of Heart Rate, Respiration, Activity, and Falls." 2013 35th Annual International Conference of the IEEE Engineering in Medical and Biology Society, pp. 6115-6118.

Chart A-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar"); Oct. 25, 2023; 19 pages.

Chart A-2 Invalidity Contentions: U.S. Pat. No. 11,051,743; Case No. 22-351-CJB (Delaware); Invalidity of U.S. Pat. No. 11,051,743 by U.S. Pat. No. 11,116,447 ("Yang"); Oct. 25, 2023; 19 pages.

Chart A-3 Invalidity Contentions: U.S. Pat. No. 11,051,743; Case No. 22-351-CJB (Delaware); Invalidity of U.S. Pat. No. 11,051,743 by U.S. Pat. No. 10,327,660 ("Gallego"); Oct. 25, 2023; 12 pages.

Chart A-3 Invalidity Contentions: U.S. Pat. No. 11,445,967; Case No. 22-351-CJB (Delaware); Invalidity of U.S. Pat. No. 11,445,967 by U.S. Pat. No. 10,327,660 ("Gallego"); Oct. 25, 2023; 7 pages.

Chart A-4 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster"); Oct. 25, 2023; 11 pages.

Chart A-4 Invalidity Contentions: U.S. Pat. No. 11,445,967; Case No. 22-351-CJB (Delaware); Invalidity of U.S. Pat. No. 11,445,967 by U.S. Pat. Pub. No. 2011/0077497 ("Oster"); Oct. 25, 2023; 6 pages.

Chart A-5 Invalidity Contentions: U.S. Pat. No. 11,051,743; Case No. 22-351-CJB (Delaware); Invalidity of U.S. Pat. No. 11,051,743 by U.S. Pat. No. 10,413,251 ("Golda"); Oct. 25, 2023; 11 pages.

Chart A-6 Invalidity Contentions: U.S. Pat. No. 11,051,743; Case No. 22-351-CJB (Delaware); Invalidity of U.S. Pat. No. 11,051,743 by U.S. Pat. No. 9,669,212 ("Mueller"); Oct. 25, 2023; 11 pages.

Chart A-7 Invalidity Contentions: U.S. Pat. No. 11,051,743; Case No. 22-351-CJB (Delaware); Invalidity of U.S. Pat. No. 11,051,743 by U.S. Pat. No. 7,206,630 ("Tarler"); Oct. 25, 2023; 12 pages.

Chart A-8 Invalidity Contentions: U.S. Pat. No. 11,051,743; Case No. 22-351-CJB (Delaware); Invalidity of U.S. Pat. No. 11,051,743 by WO 2008/005015 ("Shennib"); Oct. 25, 2023; 12 pages.

Chart A-9 Invalidity Contentions: U.S. Pat. No. 11,051,743; Case No. 22-351-CJB (Delaware); Invalidity of U.S. Pat. No. 11,051,743 by U.S. Pat. Pub. No. 2011/0009729 ("Shin"); Oct. 25, 2023; 12 pages.

Chart A-10 Invalidity Contentions: U.S. Pat. No. 11,051,743; Case No. 22-351-CJB (Delaware); Invalidity of U.S. Pat. No. 11,051,743 by WO 2003/065926 ("Ozguz"); Oct. 25, 2023; 12 pages.

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar") and U.S. Pat. No. 11,116,447 ("Yang"); Oct. 25, 2023; 24 pages.

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar"); Oct. 25, 2023; 13 pages.

Chart AA-2 Invalidity Contentions: U.S. Pat. No. 11,445,967; Case No. 22-351-CJB (Delaware); Invalidity of U.S. Pat. No. 11,445,967 by U.S. Patent No. 11, 116,447 ("Yang"); Oct. 25, 2023; 14 pages.

Chart AA-5 Invalidity Contentions: U.S. Pat. No. 11,445,967; Case No. 22-351-CJB (Delaware); Invalidity of U.S. Pat. No. 11,445,967 by U.S. Pat. No. 10,413,251 ("Golda"); Oct. 25, 2023; 6 pages.

Chart AA-6 Invalidity Contentions: U.S. Pat. No. 11,445,967; Case No. 22-351-CJB (Delaware); Invalidity of U.S. Pat. No. 11,445,967 by U.S. Pat. No. 9,669,212 ("Mueller"); Oct. 25, 2023; 6 pages.

Chart AA-7 Invalidity Contentions: U.S. Pat. No. 11,445,967; Case No. 22-351-CJB (Delaware); Invalidity of U.S. Pat. No. 11,445,967 by U.S. Pat. No. 7,206,630 ("Tarler"); Oct. 25, 2023; 7 pages.

Chart AA-8 Invalidity Contentions: U.S. Pat. No. 11,445,967; Case No. 22-351-CJB (Delaware); Invalidity of U.S. Pat. No. 11,445,967 by WO 2008/005015 ("Shennib"); Oct. 25, 2023; 6 pages.

Chart AA-9 Invalidity Contentions: U.S. Pat. No. 11,445,967; Case No. 22-351-CJB (Delaware); Invalidity of U.S. Pat. No. 11,445,967 by U.S. Pat. Pub. No. 2011/0009729 ("Shin"); Oct. 25, 2023; 6 pages.

Chart AA-10 Invalidity Contentions: U.S. Pat. No. 11,445,967; Case No. 22-351-CJB (Delaware); Invalidity of U.S. Pat. No. 11,445,967 by WO 2003/065926 ("Ozguz"); Oct. 25, 2023; 6 pages.

Chart B-1 Invalidity Contentions: U.S. Pat. No. 11,051,743 and U.S. Pat. No. 11,445,967; Case No. 22-351-CJB (Delaware); Elongated Strip With Narrowed Midsection; Oct. 25, 2023; 8 pages.

Chart B-2 Invalidity Contentions: U.S. Pat. No. 11,051,743 and U.S. Pat. No. 11,445,967; Case No. 22-351-CJB (Delaware); An Electrocardiogramactrode On Each End Of The Backing; Oct. 25, 2023; 8 pages.

Chart B-3 Invalidity Contentions: U.S. Pat. No. 11,051,743 and U.S. Pat. No. 11,445,967; Case No. 22-351-CJB (Delaware); Flexible Circuit Comprising a Pair of Circuit Traces To Couple Electrodes; Oct. 25, 2023; 8 pages.

Chart B-4 Invalidity Contentions: U.S. Pat. No. 11,051,743 and U.S. Pat. No. 11,445,967; The Case No. 22-351- CJB (Delaware); Rounded Outer Edge of Backing Ends; Oct. 25, 2023; 5 pages.

Chart B-5 Invalidity Contentions: U.S. Pat. No. 11,051,743 and U.S. Pat. No. 11,445,967; Case No. 22-351-CJB (Delaware); Conversion of Electrocardiogramanals From One Format to Another; Oct. 25, 2023; 6 pages.

Chart B-6 Invalidity Contentions: U.S. Pat. No. 11,051,743 and U.S. Pat. No. 11,445,967; Case No. 22-351-CJB (Delaware); Hydrocolloid Adhesives on a Portion of the Backing; Oct. 25, 2023; 5 pages.

Chart B-7 Invalidity Contentions: U.S. Pat. No. 11,051,743 and U.S. Pat. No. 11,445,967; Case No. 22-351-CJB (Delaware); A Patch Comprising Adhered Layers; Oct. 25, 2023; 16 pages.

Chart C-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar") and U.S. Pat. No. 11,116,447 ("Yang"); Oct. 25, 2023; 32 pages.

[Corrected] Chart C-2 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster") and U.S. Pat. No. 11,116,447 ("Yang"); Oct. 25, 2023; 22 pages.

[Corrected] Chart CC-2 Invalidity Contentions: U.S. Pat. No. 11,445,967; Case No. 22-351-CJB (Delaware); Invalidity of U.S. Patent No. by U.S. Pat. Pub. No. 2011/0077497 ("Oster") and U.S. Pat. No. 11,116,447 ("Yang"); Oct. 25, 2023; 16 pages.

Chen et al. "Monitoring Body Temperature of Newborn Infants At Neonatal Intensive Care Units Using Wearable Sensors," BodyNets 2010, Corfu Island, Greece. Sep. 10-12, 1210.

Plaintiffs Answer to Defendant's Counterclaim from Case No. 1 :22-cv-00351-CFC, *Bardy Diagnostics, Inc.* (Plaintiff) v. *Vital Connect, Inc.* (Defendant), Filed: Jun. 15, 2022, 5 pages.

Puurtinen et al., "Estimation of ECG Signal of closely separated bipolar electrodes using thorax models," Proceedings of the 26th Annual International Conference of the IEEE EMBS pp. 801-804, San Francisco, Calif., USA, Sep. 1-5, 2004, 4 pages.

Saadi et al. "Heart Rhythm Analysis Using ECG Recorded With A Novel Sternum Based Patch Technology—A Pilot Study_" Cardio technix 2013—Proceedings of the International Congress on Cardiovascular Technologies, Sep. 20, 2013.

(56) References Cited

OTHER PUBLICATIONS

Saeed et al., "A Scalable Wireless Body Area Sensor Network for Health-Care Monitoring," Jun. 2009, 4 pages.

Sapoznikov, Dan et al., "Comparison of Different Methodologies of Heart Rate Variability Analysis," Department of Cardiology, Hadassah University Hospital, P.O.B. 12000, Ein Kerem, Jerusalem 91120, Israel (1993).

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Skretting et al., "Improved Huffman Coding Using Recursive Splitting," NORSIG, Jan. 1, 1999.

Sleepview, URL <http://www.clevemed.com/sleepview/overview.shtml> (Web page cached on Sep. 4, 2013.).

Smith, Jawbone Up, URL <http://www.businessinsider.com/fitbit-flex-vs-jawbone-up-2013-5?op=1> (Jun. 1, 2013).

Toth et al., U.S. Appl. No. 61/832,131, filed Jun. 6, 2013, 82 pages.

Trägårdh et al., How Many ECG Leads Do We Need? Cardiology Clinics. Aug. 2006; 24(3): 317-30, vii. doi: 10.1016/j.ccl.2006.04.005. PMID: 16939826; 14 pages.

Varicrad-Kardi Software User's Manual Rev_ 1.1, Jul. 8, 2009 (Jul. 8, 2009), XP002757888, retrieved from the Internet: URL:http://www.ehrlich.tv/KARDiVAR-Software.pdf [retrieved on May 20, 2016].

Vishnubhotla, "Pre-processing of ECG signals for ambulatory use," Jan. 2009; 5 pages.

Voss, A. et al., "Linear and Nonlinear Methods for Analyses of Cardiovascular Variability in Bipolar Disorders," Bipolar Disorders, vol. 8, No. 5 p. 1, Oct. 1, 2006, pp. 441-452, XP55273826, DK ISSN: 1398-5647, DOI: 10.1111/.1399-5618 -2006 .00364 x.

Wallot et al., "Using Complexity Metrics With R-R Intervals And BPM Heart Rate Measures," Frontiers in Physiology, vol. 4, Article 211, pp. 1-8, Aug. 13, 2013. 2013.

Wolf, "The Data-Driven Life," New York Times Magazine, Apr. 28, 2010, 13 pages.

Zio Event Card, URL <http://www.irhythmtech.com/zio-solution/zio-event/> (Web page cached on Mar. 11, 2013.).

Zio Patch System, URL <http://www.irhythmtech.com/zio-solution/zio-system/index.html> (Web page cached on Sep. 8, 2013.).

*Bardy Diagnostics, Inc.*, Plaintiff v. *Irhythm Technologies, Inc.*; The United States District Court for the District of Delaware; Complaint against iRhythm Technologies; filed Dec. 10, 2024.

Exhibits 1-13 for *Bardy Diagnostics, Inc.*, Plaintiff v. *Irhythm Technologies, Inc.*; The United States District Court for the District of Delaware; Complaint against iRhythm Technologies; filed Dec. 10, 2024.

*Bardy Diagnostics, Inc.*, Plaintiff v. *Irhythm Technologies, Inc.*; The United States District Court for the District of Delaware; C.A. No. 24-1355-RGA; First Amended Complaint against iRhythm Technologies; filed Dec. 26, 2024.

Exhibits 1-15 for *Bardy Diagnostics, Inc.*, Plaintiff v. *Irhythm Technologies, Inc.*; The United States District Court for the District of Delaware; C.A. No. 24-1355-RGA; First Amended Complaint against iRhythm Technologies; filed Dec. 26, 2024.

*Bardy Diagnostics, Inc.*, Plaintiff v. *Irhythm Technologies, Inc.*; The United States District Court for the District of Delaware; C.A. No. 24-1355 (JDW); Defendant iRhythm Technologies, Inc.'s Counterclaim and Answer to Plaintiff Bardy Diagnostics, Inc.'s First Amended Complaint; filed Mar. 3, 2025.

Exhibits 1-10 for *Bardy Diagnostics, Inc.*, Plaintiff v. *Irhythm Technologies, Inc.*; The United States District Court for the District of Delaware; C.A. No. 24-1355 (JDW); Defendant iRhythm Technologies, Inc.'s Counterclaim and Answer to Plaintiff Bardy Diagnostics, Inc.'s First Amended Complaint; filed Mar. 3, 2025.

*Vital Connect, Inc.* v. *Bardy Diagnostics, Inc.*, USPTO Patent Trial & Appeal Board—Patent Owner's Preliminary Response, Case No. IPR2023-00381 for U.S. Pat. No. 11,051,743, dated Apr. 24, 2023. 53 pages.

*Vital Connect, Inc.* v. *Bardy Diagnostics, Inc.*, USPTO Patent Trial & Appeal Board—Decision Denying Institution of Inter Partes Review 35 U.S.C. § 314, Case No. IPR2023-00381 for U.S. Pat. No. 11,051,743, dated Jul. 11, 2023. 21 pages.

*Vital Connect, Inc.* v. *Bardy Diagnostics, Inc.*, USPTO Patent Trial & Appeal Board—Order, Case No. IPR2023-00381 for U.S. Pat. No. 11,051,743, dated Oct. 3, 2023. 3 pages.

*Vital Connect, Inc.* v. *Bardy Diagnostics, Inc.*, USPTO Patent Trial & Appeal Board—Declaration of Dr. Per Reinhall, Ph.D, Case No. IPR2023-00381 for U.S. Pat. No. 11,051,743, dated Apr. 21, 2023. 28 pages.

Bardy Diagnostics Statutory Disclaimer Under 35 U.S.C. 253(a) and 37 C.F.R. § 1.321(a) for U.S. Pat. No. 11,051,743, dated Apr. 21, 2023. 2 pages.

Defendant's Answer to First Amended Complaint, Defenses, and Counterclaim, 1 :22-cv-00351-CJB, *BardyDiagnostics, Inc.* v. *Vital Connect, Inc.* (D. Del.), filed Jan. 24, 2023 (227 pages).

Non-Final Office Action from U.S. Appl. No. 18/933,792, mailed Mar. 20, 2025. 27 pages.

*Irhythm, Inc.* v. *Welch Allyn, Inc.*, Petition for Inter Partes Review Under 35 U.S.C. § 312 and 37 C.F.R. § 42.104, Case No. IPR2025-01081 for U.S. Pat. No. 8,630,699, dated Jun. 3, 2025. 81 pages.

501(k) Summary of Safety & Effectiveness, 501(k) No. K083287, AVIVO Mobile Patient Management System, dated Nov. 6, 2008 ("AVIVO 501(k)").

510(k) Summary of Safety & Effectiveness, 510(k) No. K043604, VivoMetrics, Inc. LifeShirt™ Real-Time, Apr. 29, 2005.

AAMI, Ambulatory ElectrocardiogramaAMI EC38: 1998 (1998).

AAMI, Cardiac monitors, heart rate meters, and alarms, ANSI/AAMI EC13:2002 (2002).

AAMI, Diagnostic electrocardiogramI EC11:1991 (1991).

Ajay Bharadwaj & Umanath Kamath, Accurate ECG signal processing, CA: Cypress Semiconductor (Feb. 2011).

Am. Coll. Cardiology, Am. Heart Ass'n Task Force on Practice Guidelines, ACC/AHA Guidelines for Ambulatory Electrocardiogrammary and Recommendations, 100 CIRCULATION 886 (1999), available at <https://www.ahajournals.org/doi/full/10.1161/0.

Aoife Morrin et al., Electrochemical Characterization of Commercial and Home-Made Screen-Printed Carbon Electrodes, 36 Anal. Letters, 2021 (2003).

Bert Gyselinckx & Sofie Pollin, Wireless sensor nodes: potential and challenges, Embedded Systems West Conference (2007).

Bert Gyselinckx et al., Human++: Autonomous Wireless Sensors for Body Area Networks, IEEE 2005 Custom Integrated Circuits Conference.

Bert-Uwe Köhler et al., The Principles of Software QRS Detection, IEEE Eng. Med. & Bio. (2002).

Brian Burkhardt, The Future of Electrocardiogrametry Systems, Int'l Telemetering Conference Proceedings (2004).

Bruce R. Bowman & Edward Schuck, Medical Instruments and Devices Used in the Home, CRC Press LLC (2000). (BOOK—Introduction and Preface only)(Full contents available at: https://www.google.com/url sa=t&rct=j&q=&esrc=s&source=web&cd=&ved=2ahUKEwjwv6b079OPAxVHL9AFHdajHTIQFnoECBwQAQ&url=https%3A%2F%2Fbiblioseb.files.wordpress.com%2F2018%2F03%2Fbiomedical-engineering-handbook-j-d-bronzino.pdf&usg=AOvVaw2egUNjtqQgxyMFMrLNqB2X&opi=89978449).

C.J. Harland et al., Electric Potential Probes—New Directions in the Remote Sensing of the Human Body, 13 Meas. Sci. Tech. 163 (2002).

Claus F Nielsen et al., Strategic Intelligence Monitor on Personal Health Systems, Phase 2, JR Scientific and Policy Reports, Country Study: Denmark (2013).

Corventis, AVIVO® Mobile Patient Management System, https://corventis.com/US/AVIVO.asp, Dec. 16, 2009 ("AVIVO Webpage").

Corventis, AVIVO™ Mobile Patient Management System, Instructions for Use (2010) ("AVIVO —Instructions for Use").

Creative Materials, Medical Device Specialty Inks and Films, available at <http://www.creativematerials.com/lit-erature/medical_device.pdf>, archived at Wayback Machine (<https://web.archive.org/web/20060508230449/http://www.creativematerials.com/liter.

Daniel E. Becker, Fundamentals of Electrocardiogramterpretation, 53 Anesthesia Progress 53, 53 (2006).

(56)                  References Cited

OTHER PUBLICATIONS

David Prutchi & Michael Norris, Design and Development of Medical Electronic Instrumentation (2005).

Defendant's Preliminary Invalidity Contentions, C.A. No. 1:24-cv-01355-JDW filed Jul. 24, 2025.

Devices@FDA: Dexcom STS Continuous Monitors, U.S. Food & Drug Admin. (2005), available at <https://www.accessdata.fda.gov/scripts/cdrh/devicesatfda/index.cfm?db=pma&id=320251>.

Dorthe B. Nielsen et al., Automatic QRS Complex Detection Algorithm Designed for a Novel, Wearable, Wireless Electrocardiogram Recording Device, 34 Ann. Int'l Conf. of the IEEE EMBS, San Diego, CA USA, 28 Aug. 28-Sep. 1, 2012.

Edward K. Chung, Ambulatory Electrocardiogramalter Monitor Electrocardiogramabstract Only).

Euan A. Ashley & Josef Niebauer, Cardiology Explained (2004), available at <https://www.ncbi.nlm.nih.gov/books/NBK2204/>. (Abstract Only).

Exhibit A: Invalidity of U.S. Pat. No. 12,171,562 by AVIVO ("Corventis AVIVO System"); 4,081 pages.

Exhibit B: Invalidity of U.S. Pat. No. 12,161,473 by the AVIVO System ("Corventis AVIVO System"); 4,322 pages.

Exhibit C: Invalidity of U.S. Pat. No. 12,285,261 by AVIVO ("the Corventis AVIVO System"); 3,049 pages.

Exhibit D: Invalidity of U.S. Pat. No. 12,310,735 by the AVIVO System ("Corventis AVIVO Mobile Patient Management System"); 3,456 pages.

Exhibit E: State of the Art References for U.S. Pat. Nos. 12,161,473, 12,171,562, 12,285,261, and 12,310,735; 11 pages.

F. Lateef et al., The V-Quick patch versus the standard 12-lead ECG system: Time is the essence, International Journal of Emergency Medicine. 1:43-48 (2008).

Gautham Kalahasty et al., A Brief History of Remote Cardiac Monitoring, 5 Cardiac Electrophysiology Clinics 275 (2013).

https://web.archive.org/web/20091216175134/https://corventis.com/US/AVIVO.asp (available at least by Dec. 16, 2009) ("AVIVO Webpage").

J. Muhlsteff et al., Wearable approach for continuous ECG—and Activity Patient-Monitoring, 1 26th Proc. Int'l Conf. of IEEE Eng'g in Med. & Biol. Soc'y 2184 (2004).

J. Terry Caves et al., Sampled Analog Filtering Using Switched Capacitors as Resistor Equivalents, 12 IEEE Journal of Solid—State Circuits 592 (1977).

Jaehoon Kim, Implanted Antennas for Medical Wireless Communications: Characterizations, Designs and Performance Evaluations (2005) (Ph. D. dissertation, Univ. Cal. L.A.).

Jameco Electronics, 8-Pin, 8-Bit CMOS Microcontrollers Data Sheet, <https://web.archive.org/web/20031126132956/http://jameco.com/Ja meco/Products/ProdDS/200475.pdf> (available as of Nov. 26, 2003).

James Welch, Farzin Guilak, & Steven D. Baker, A Wireless ECH Smart Sensor for Broad Application in Life Threatening Event Detection, Proceedings of the 25th Annual Int'l Conf. of the IEEE EMBS, San Francisco, CA (Sep. 1-5, 2004).

Jan Adamec & Richard Adamec, ECG Holter, Guide to Electrocardiogramterpretation (2008).

Jiapu Pan & Willis J. Tompkins, A Real-Time QRS Detection Algorithm, BME-22 IEEE Transactions On Biomed. Eng'g 230 (1985).

Joel Morganroth, Ambulatory Holter Electrocardiogramologies and Clinical Uses, Anals. of Internal. Med. (1985). (Abstract Only).

Klaus-Peter Hoffmann & Roman Ruff, Flexible dry surface- electrodes for ECG long-term monitoring 5739 (2007).

Lawrence R. Dallett & William E. Donaldson, Plastics and Adhesives: A Guide to Their Physical Properties and Uses, U.S. Dep't of Com. (1956).

Linda S. Baas et al., Accuracy of the Precordial V-Quick® Patch in Persons with Cardiac or Pulmonary Disease, 24 The Journal of Emergency Medicine 2, pp. 131-139 (2003). (Abstract Only).

Maeona K. Jacobs, Sources of Measurement Error in Noninvasive Electronic Instrumentation, 13 Nursing Clinics N. Am. 573 (1978).

Majd AlGhatrif & Joseph Lindsay, A Brief Review: History to Understand Fundamentals of Electrocardiograma J. Community Hosp. & Internal Med. Persps. 14383 (2012).

Matts Ahlsen et al., Service-Oriented Middleware Architecture for Mobile Personal Health Monitoring, Int'l Conf. On Wireless Mobile Comm. and Healthcare, Berlin, Heidelberg: Springer Berlin Heidelberg (Oct. 2011).

Medtronic Monitoring Inc., XOH-PIIX, Equipment: Medtronic Monitoring, Inc., —PIIX; External Photos Report, FCC.report (Feb. 18, 2010), https://fcc.report/FCC-ID/XOH-PIIX/1242847.pdf ("PiiX External").

Medtronic Monitoring Inc., XOH-PIIX, Equipment: Medtronic Monitoring, Inc.,—PIIX; Internal Photos Report, FCC.report (Feb. 18, 2010), https://fcc.report/FCC-ID/XOH-PIIX/1242848.pdf ("PiiX Internal").

Michael R. Neuman, Biopotential Electrodes, Medical Instrumentation (3d ed. 1998).

Mike Cadogan, Norman J. Holter (2022), available at <https://litfl.com/norman-j-holter/>.

N.V. Thakor & J.G Webster, Electrode studies for the long-term ambulatory ECG, MED. & BIOL. ENG. & COMPUT. (1985). (Abstract Only).

Nihon Kohden, 4 or 8 Patient Telemetry Monitoring, <http://www.nihonkohden.com/products/monitor/wep4200.html>, Oct. 30, 2005 ("Nihon Kohden Webpage—Telemetry Systems").

Nihon Kohden, Patient Monitoring, <http:/www.nihonkohden.com/products/monitor/index.html>, Oct. 30, 2005 ("Nihon Kohden Webpage—Overview").

Nihon Kohden, Transmitters for Life Scope monitors, <http://www.nihonkohden.com/products/monitor/transmitters.html>, Oct. 30, 2005 ("Nihon Kohden Webpage —Transmitters").

Nitish V. Thakor, From Holter Monitors to Automatic Defibrillators: Developments in Ambulatory Arrhythmia Monitoring, IEEE Transactions On Biomed. Eng'g, 770 (1984).

P.J.B. Hubner, Which Disposable Chest Electrode?, British Med. J., 507 (Aug. 30, 1969).

Patrick J. Nolan, Sterile Medical Device Package Development, Standard Handbook of Biomedical Eng'g & Design (2004).

R.S. Khandpur, Printed Circuit Boards: Design, Fabrication, Assembly, and Testing (2006).

Robert A. Millikan & E.S. Bishop, Elements of Electricity (1917).

Robert P. Grant, Spatial Vector Electrocardiogra.

Roubik Gregorian & William E. Nicholson, Jr., A Switched- Capacitor High-Pass Filter, 27 IEEE Transactions On Circuits and Sys. 226 (1980).

Stephane Donnay, Human++ Wireless Body-area networks (WBAN) for health monitoring applications, ESF Workshop on Wireless Sensor Networks (Apr. 1-2, 2004).

Steven L. Higgins, A Novel Patch for Heart Rhythm Monitoring: is the Holter Monitor Obsolete?, Future Cardiology 9:3, 325-333 (2013). (Abstract Only).

Thermo-Electron and VivoMetrics Deliver the First Real-Time Monitoring Ensemble, EMS1, Apr. 10, 2006.

Tilak Shah, Polyurethane Thin-Film Welding for Medical Device Applications, Med. Device and Diagnostic Indus. (2002).

Tsuyoshi Kato et al., An Application of Capacitive Electrode for Detecting Electrocardiogram of Neonates and Infants, 2006 Int'l Conf. of the IEEE Eng'g Med. & BIO. (2006).

TUV Rheinland of North America, Inc., PiiX Emmissions Test Report, Apr. 6, 2009.

V. Trend et al., Are ECG Welsh cup electrodes effectively cleaned?, 14 J. Hosp. Infection 325 (1989).

V.W. Greene, Reuse of Disposable Medical Devices: Historical and Current Aspects, 7 Infection Control & Hosp. Epidemiology 508 (1986). (Abstract Only).

VPMS Components, V Patch Medical Systems—Next generation Wireless ECG Telemetry, https://www.vpatchmedical.com/pages/vpms-components.php (Jan. 14, 2011).

Zeli Gao, et al., Design of ECG signal acquisition and processing system, 2012 International Conference On Biomedical Engineering and Biotechnology, IEEE, 2012, 762.

(56) References Cited

OTHER PUBLICATIONS

Biospace.com, "Proteus Biomedical, Inc. Raises $25M; Gets FDA 510(k) Clearance for Raisin Personal Monitor", BioSpace, URL: <https://www.biospace.com>. (Apr. 21, 2010). 8 pages.

Catherwood et al., "ECG Motion Artefact Reduction Improvements of a Chest-Based Wireless Patient Monitoring System", Computing in Cardiology (2010), vol. 37, pp. 557-560.

Dolan, Brian, "Isansys Secures CE Mark for Wearable Wireless Medical Sensor", MobiHealth News, (Apr. 18, 2012). 15 pages.

McAdams et al., "Wearable Sensor Systems: The Challenges", 33rd Annual International Conference of the IEEE in Medicine and Biology Society (2011), Boston, Massachusetts, pp. 3648-3651.

* cited by examiner

80

100

130

140

150

160

170

180

MOISTURE-RESISTANT ELECTROCARDIOGRAPHY MONITOR

PRIORITY CLAIM AND CROSS-REFERENCE TO RELATED APPLICATIONS

This application is a continuation of U.S. patent application Ser. No. 19/098,670, filed Apr. 2, 2025, titled MOISTURE-RESISTANT ELECTROCARDIOGRAPHY MONITOR, which is a continuation of U.S. patent application Ser. No. 18/318,641, filed May 16, 2023, titled MOISTURE-RESISTANT ELECTROCARDIOGRAPHY MONITOR, which is a continuation of U.S. patent application Ser. No. 17/959,174, filed Oct. 3, 2022, titled MULTICOMPONENT ELECTROCARDIOGRAPHY MONITOR, which is a continuation of U.S. patent application Ser. No. 16/782,951, filed Feb. 5, 2020, titled MULTICOMPONENT ELECTRO-CARDIOGRAPHY MONITOR, which is a continuation of U.S. patent application Ser. No. 16/404,562, filed May 6, 2019, titled MULTIPART ELECTROCARDIOGRAPHY MONITOR OPTIMIZED FOR CAPTURING LOW AMPLITUDE CARDIAC ACTION POTENTIAL PROPAGATION, which is a continuation of U.S. patent application Ser. No. 16/174,122, filed Oct. 29, 2018, titled AMBULATORY ELECTROCARDIOGRAPHY MONITOR OPTIMIZED FOR CAPTURING LOW AMPLITUDE CARDIAC ACTION POTENTIAL PROPAGATION, which is a continuation of U.S. patent application Ser. No. 15/645,708, filed Jul. 10, 2017, titled EXTENDED WEAR ELECTRO-CARDIOGRAMY MONITOR OPTIMIZED FOR CAPTURING LOW AMPLITUDE CARDIAC ACTION POTENTIAL PROPAGATION, which is a continuation of U.S. patent application Ser. No. 14/488,230, filed Sep. 16, 2014, titled AMBULATORY ELECTROCARDIOGRAPHY MONITORING PATCH OPTIMIZED FOR CAPTURING LOW AMPLITUDE CARDIAC ACTION POTENTIAL PROPAGATION, which is a continuation in-part of U.S. patent application Ser. No. 14/080,725, filed Nov. 14, 2013, titled EXTENDED WEAR AMBULATORY ELECTROCARDIOGRAPHY AND PHYSIOLOGICAL SENSOR MONITOR, which claims priority to U.S. Provisional Patent App. No. 61/882,403, filed Sep. 25, 2013, titled LONG-TERM WEARABLE PHYSIOLOGICAL MONITOR. The entire contents of these applications are incorporated by reference herein in their entirely and relied upon.

FIELD

This application relates in general to electrocardiographic monitoring and, in particular, to a moisture-resistant electrocardiography monitor.

BACKGROUND

The first electrocardiogram (ECG) was invented by a Dutch physiologist, Willem Einthoven, in 1903, who used a string galvanometer to measure the electrical activity of the heart. Generations of physicians around the world have since used ECGs, in various forms, to diagnose heart problems and other potential medical concerns. Although the basic principles underlying Dr. Einthoven's original work, including his naming of various waveform deflections (Einthoven's triangle), are still applicable today, ECG machines have evolved from his original three-lead ECG, to ECGs with unipolar leads connected to a central reference terminal starting in 1934, to augmented unipolar leads beginning in 1942, and finally to the 12-lead ECG standardized by the American Heart Association in 1954 and still in use today. Further advances in portability and computerized interpretation have been made, yet the electronic design of the ECG recording apparatuses has remained fundamentally the same for much of the past 40 years.

Essentially, an ECG measures the electrical signals emitted by the heart as generated by the propagation of the action potentials that trigger depolarization of heart fibers. Physiologically, transmembrane ionic currents are generated within the heart during cardiac activation and recovery sequences. Cardiac depolarization originates high in the right atrium in the sinoatrial (SA) node before spreading leftward towards the left atrium and inferiorly towards the atrioventricular (AV) node. After a delay occasioned by the AV node, the depolarization impulse transits the Bundle of His and moves into the right and left bundle branches and Purkinje fibers to activate the right and left ventricles.

During each cardiac cycle, the ionic currents create an electrical field in and around the heart that can be detected by ECG electrodes placed on the skin. Cardiac electrical activity is then visually represented in an ECG trace by PQRSTU-waveforms. The P-wave represents atrial electrical activity, and the QRSTU components represent ventricular electrical activity. Specifically, a P-wave represents atrial depolarization, which causes atrial contraction.

P-wave analysis based on ECG monitoring is critical to accurate cardiac rhythm diagnosis and focuses on localizing the sites of origin and pathways of arrhythmic conditions. P-wave analysis is also used in the diagnosis of other medical disorders, including imbalance of blood chemistry. Cardiac arrhythmias are defined by the morphology of P-waves and their relationship to QRS intervals. For instance, atrial fibrillation (AF), an abnormally rapid heart rhythm, can be confirmed by an absence of P-waves and an irregular ventricular rate. Similarly, sinoatrial block is characterized by a delay in the onset of P-waves, while junctional rhythm, an abnormal heart rhythm resulting from impulses coming from a locus of tissue in the area of the AV node, usually presents without P-waves or with inverted P-waves. Also, the amplitudes of P-waves are valuable for diagnosis. The presence of broad, notched P-waves can indicate left atrial enlargement. Conversely, the presence of tall, peaked P-waves can indicate right atrial enlargement. Finally, P-waves with increased amplitude can indicate hypokalemia, caused by low blood potassium, whereas P-waves with decreased amplitude can indicate hyperkalemia, caused by elevated blood potassium.

Cardiac rhythm disorders may present with lightheadedness, fainting, chest pain, hypoxia, syncope, palpitations, and congestive heart failure (CHF), yet rhythm disorders are often sporadic in occurrence and may not show up in-clinic during a conventional 12-second ECG. Continuous ECG monitoring with P-wave-centric action potential acquisition over an extended period is more apt to capture sporadic cardiac events. However, recording sufficient ECG and related physiological data over an extended period remains a significant challenge, despite an over 40-year history of ambulatory ECG monitoring efforts combined with no appreciable improvement in P-wave acquisition techniques since Dr. Einthoven's original pioneering work over a 110 years ago.

Electrocardiographic monitoring over an extended period provides a physician with the kinds of data essential to identifying the underlying cause of sporadic cardiac conditions, especially rhythm disorders, and other physiological events of potential concern. A 30-day observation period is considered the "gold standard" of monitoring, yet a 14-day observation period is currently pitched as being achievable by conventional ECG monitoring approaches. Realizing a 30-day observation period has proven unworkable with existing ECG monitoring systems, which are arduous to employ; cumbersome, uncomfortable and not user-friendly to the patient; and costly to manufacture and deploy. Still, if a patient's ECG could be recorded in an ambulatory setting over a prolonged time periods, particularly for more than 14 days, thereby allowing the patient to engage in activities of daily living, the chances of acquiring meaningful medical information and capturing an abnormal event while the patient is engaged in normal activities are greatly improved.

The location of the atria and their low amplitude, low frequency content electrical signals make P-waves difficult to sense, particularly through ambulatory ECG monitoring. The atria are located posteriorly within the chest, and their physical distance from the skin surface adversely affects current strength and signal fidelity. Cardiac electrical potentials measured dermally have an amplitude of only one-percent of the amplitude of transmembrane electrical potentials. The distance between the heart and ECG electrodes reduces the magnitude of electrical potentials in proportion to the square of change in distance, which compounds the problem of sensing low amplitude P-waves. Moreover, the tissues and structures that lie between the activation regions within the heart and the body's surface alter the cardiac electrical field due to changes in the electrical resistivity of adjacent tissues. Thus, surface electrical potentials, when even capable of being accurately detected, are smoothed over in aspect and bear only a general spatial relationship to actual underlying cardiac events, thereby complicating diagnosis. Conventional 12-lead ECGs attempt to compensate for weak P-wave signals by monitoring the heart from multiple perspectives and angles, while conventional ambulatory ECGs primarily focus on monitoring higher amplitude ventricular activity that can be readily sensed. Both approaches are unsatisfactory with respect to the P-wave and the accurate, medically actionable diagnosis of the myriad cardiac rhythm disorders that exist.

Additionally, maintaining continual contact between ECG electrodes and the skin after a day or two of ambulatory ECG monitoring has been a problem. Time, dirt, moisture, and other environmental contaminants, as well as perspiration, skin oil, and dead skin cells from the patient's body, can get between an ECG electrode's non-conductive adhesive and the skin's surface. These factors adversely affect electrode adhesion and the quality of cardiac signal recordings. Furthermore, the physical movements of the patient and their clothing impart various compressional, tensile, bending, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, multi-week or multi-month monitoring can be performed by implantable ECG monitors, such as the Reveal LINQ insertable cardiac monitor, manufactured by Medtronic, Inc., Minneapolis, MN. This monitor can detect and record paroxysmal or asymptomatic arrhythmias for up to three years. However, like all forms of implantable medical device (IMD), use of this monitor requires invasive surgical implantation, which significantly increases costs; requires ongoing follow up by a physician throughout the period of implantation; requires specialized equipment to retrieve monitoring data; and carries complications attendant to all surgery, including risks of infection, injury or death.

Holter monitors are widely used for extended ECG monitoring. Typically, they are often used for only 24-48 hours. A typical Holter monitor is a wearable and portable version of an ECG that include cables for each electrode placed on the skin and a separate battery-powered ECG recorder. The leads are placed in the anterior thoracic region in a manner similar to what is done with an in-clinic standard ECG machine using electrode locations that are not specifically intended for optimal P-wave capture. The duration of monitoring depends on the sensing and storage capabilities of the monitor. A "looping" Holter (or event) monitor can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest precludes a patient from replacing or removing the sensing leads and usually involves moving the patient from the physician office to a specialized center within the hospital or clinic.

U.S. Pat. No. 8,460,189, to Libbus et al. ("Libbus") discloses an adherent wearable cardiac monitor that includes at least two measurement electrodes and an accelerometer. The device includes a reusable electronics module and a disposable adherent patch that includes the electrodes. ECG monitoring can be conducted using multiple disposable patches adhered to different locations on the patient's body. The device includes a processor configured to control collection and transmission of data from ECG circuitry, including generating and processing of ECG signals and data acquired from two or more electrodes. The ECG circuitry can be coupled to the electrodes in many ways to define an ECG vector, and the orientation of the ECG vector can be determined in response to the polarity of the measurement electrodes and orientation of the electrode measurement axis. The accelerometer can be used to determine the orientation of the measurement electrodes in each of the locations. The ECG signals measured at different locations can be rotated based on the accelerometer data to modify amplitude and direction of the ECG features to approximate a standard ECG vector. The signals recorded at different locations can be combined by summing a scaled version of each signal. Libbus further discloses that inner ECG electrodes may be positioned near outer electrodes to increase the voltage of measured ECG signals. However, Libbus treats ECG signal acquisition as the measurement of a simple aggregate directional data signal without differentiating between the distinct kinds of cardiac electrical activities presented with an ECG waveform, particularly atrial (P-wave) activity.

The ZIO XT Patch and ZIO Event Card devices, manufactured by iRhythm Tech., Inc., San Francisco, CA, are wearable monitoring devices that are typically worn on the upper left pectoral region to respectively provide continuous and looping ECG recording. The location is used to simulate surgically implanted monitors, but without specifically enhancing P-wave capture. Both of these devices are prescription-only and for single patient use. The ZIO XT Patch device is limited to a 14-day period, while the electrodes only of the ZIO Event Card device can be worn for up to 30 days. The ZIO XT Patch device combines both electronic recordation components and physical electrodes into a unitary assembly that adheres to the patient's skin. The ZIO XT Patch device uses adhesive sufficiently strong to support the weight of both the monitor and the electrodes over an extended period and to resist disadherence from the patient's body, albeit at the cost of disallowing removal or relocation during the monitoring period. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of cardiac electrical potential signals, especially atrial (P-wave) signals.

Therefore, a need remains for a low cost extended wear continuously recording ECG monitor attuned to capturing low amplitude cardiac action potential propagation for arrhythmia diagnosis, particularly atrial activation P-waves, and practicably capable of being worn for a long period of time, especially in patient's whose breast anatomy or size can interfere with signal quality in both women and men.

SUMMARY

Physiological monitoring can be provided through a lightweight wearable monitor that includes two components, a flexible extended wear electrode patch and a reusable monitor recorder that removably snaps into a receptacle on the electrode patch. The wearable monitor sits centrally (in the midline) on the patient's chest along the sternum oriented top-to-bottom. The ECG electrodes on the electrode patch are tailored to be positioned axially along the midline of the sternum for capturing action potential propagation in an orientation that corresponds to the aVF lead used in a conventional 12-lead ECG that is used to sense positive or upright P-waves. The placement of the wearable monitor in a location at the sternal midline (or immediately to either side of the sternum), with its unique narrow "hourglass"-like shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms.

Moreover, the electrocardiography monitor offers superior patient comfort, convenience and user-friendliness. The electrode patch is specifically designed for ease of use by a patient (or caregiver); assistance by professional medical personnel is not required. The patient is free to replace the electrode patch at any time and need not wait for a doctor's appointment to have a new electrode patch placed. Patients can easily be taught to find the familiar physical landmarks on the body necessary for proper placement of the electrode patch. Empowering patients with the knowledge to place the electrode patch in the right place ensures that the ECG electrodes will be correctly positioned on the skin, no matter the number of times that the electrode patch is replaced. In addition, the monitor recorder operates automatically and the patient only need snap the monitor recorder into place on the electrode patch to initiate ECG monitoring. Thus, the synergistic combination of the electrode patch and monitor recorder makes the use of the electrocardiography monitor a reliable and virtually foolproof way to monitor a patient's ECG and physiology for an extended, or even open-ended, period of time.

In one embodiment, a moisture-resistant electrocardiography monitor is provided. The monitor includes an electrocardiography monitor recorder and an extended wear electrode patch. The electrocardiography monitor recorder includes a wearable housing molded out of one or more materials and sealed against moisture; a plurality of electrical contacts protruding from the wearable housing; a seal coupling positioned on the wearable housing and surrounding the electrical contacts; and electronic circuitry provided within the wearable housing. The electronic circuitry includes an electrocardiographic front end circuit under a control of a micro-controller and adapted to sense cardiac electrical potential differentials through electrocardiographic electrodes via some of the electrical contacts, which are provided to the micro-controller as an analog signal; the micro-controller configured to sample the analog signal; and a memory electrically interfaced with the micro-controller and operable to store the samples. The extended wear electrode patch includes a flexible backing including a plurality of adhesive contact surfaces; the electrocardiographic electrodes, each included on one of the adhesive contact surfaces; a receptacle affixed to a non-contacting surface of the flexible backing into which the wearable housing can be removable secured, the receptacle including a compartment within which a component interfaced to the electronic circuitry is positioned via some of the electrical contacts; a plurality of electrical pads positioned on the receptacle, each of the pads configured to interface with one of the electrical contacts when the wearable housing is secured within the receptacle; and a moisture-resistant seal formed on the receptacle and surrounding the electrical pads, wherein the moisture-resistant seal mates the seal coupling when the wearable housing is secured within the receptacle.

In a further embodiment, a moisture-resistant patient-interfacing electrocardiography monitor is provided. The monitor includes an electrocardiography monitor recorder and an extended wear electrode patch. The electrocardiography monitor recorder includes a wearable housing molded out of one or more materials and sealed against moisture; a waterproof patient-operable tactile feedback button positioned on an outside of the wearable housing; a plurality of electrical contacts protruding the wearable housing; a seal coupling positioned on the wearable housing and surrounding the electrical contacts; and electronic circuitry provided within the wearable housing. The electronic circuitry includes an electrocardiographic front end circuit under a control of a micro-controller and adapted to sense cardiac electrical potential differentials through electrocardiographic electrodes via some of the electrical contacts, which are provided to the micro-controller as an analog signal; the micro-controller configured to sample the analog signal; and a memory electrically interfaced with the micro-controller and operable to store the samples. The extended wear electrode patch includes: a flexible backing including a plurality of adhesive contact surfaces; the electrocardiographic electrodes, each included on one of the adhesive contact surfaces; a receptacle affixed to a non-contacting surface of the flexible backing into which the wearable housing can be removable secured, the receptacle including a compartment within which a battery, wherein the electronic circuitry is powered by the battery via at least some of the electrical contacts; a plurality of electrical pads positioned on the receptacle, each of the pads configured to interface with one of the electrical contacts when the wearable housing is secured within the receptacle; and a moisture-resistant seal formed on the receptacle and surrounding the electrical pads, wherein the moisture-resistant seal mates the seal coupling when the wearable housing is secured within the receptacle.

The monitoring patch is especially suited to the female anatomy, although also easily used over the male sternum. The narrow longitudinal midsection can fit nicely within the inter-mammary cleft of the breasts without inducing discomfort, whereas conventional patch electrodes are wide and, if adhered between the breasts, would cause chafing, irritation, discomfort, and annoyance, leading to low patient compliance.

In addition, the foregoing aspects enhance comfort in women (and certain men), but not irritation of the breasts, by placing the monitoring patch in the best location possible for optimizing the recording of cardiac signals from the atrium, particularly P-waves, which is another feature critical to proper arrhythmia and cardiac rhythm disorder diagnoses.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
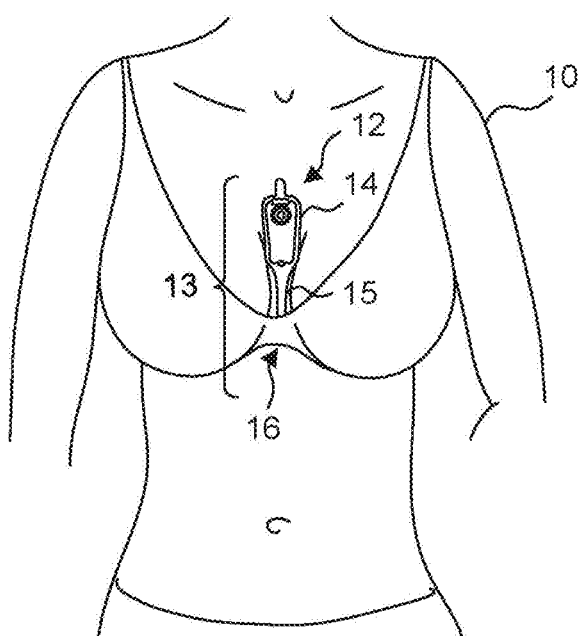
FIGS. 1 and 2 are diagrams showing, by way of examples, an extended wear electrocardiography monitor, including an extended wear electrode patch, in accordance with one embodiment, respectively fitted to the sternal region of a female patient and a male patient.
Figure 2:
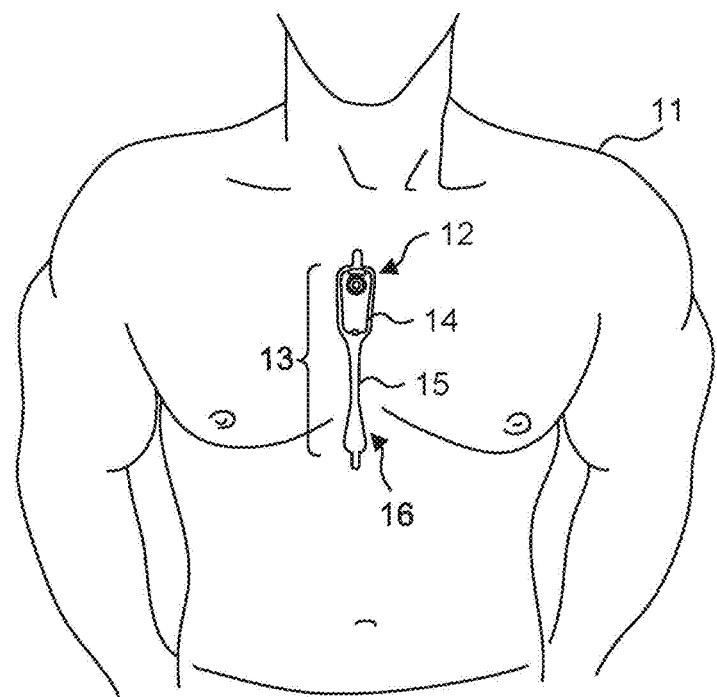

ECG and physiological monitoring can be provided through a wearable ambulatory monitor that includes two components, a flexible extended wear electrode patch and a removable reusable (or single use) monitor recorder. Both the electrode patch and the monitor recorder are optimized to capture electrical signals from the propagation of low amplitude, relatively low frequency content cardiac action potentials, particularly the P-waves generated during atrial activation. FIGS. 1 and 2 are diagrams showing, by way of examples, an extended wear electrocardiography monitor 12, including a monitor recorder 14, in accordance with one embodiment, respectively fitted to the sternal region of a female patient 10 and a male patient 11. The wearable monitor 12 sits centrally, positioned axially along the sternal midline 16, on the patient's chest along the sternum 13 and oriented top-to-bottom with the monitor recorder 14 preferably situated towards the patient's head. In a further embodiment, the orientation of the wearable monitor 12 can be corrected post-monitoring, as further described infra, for instance, if the wearable monitor 12 is inadvertently fitted upside down.

The electrode patch 15 is shaped to fit comfortably and conformal to the contours of the patient's chest approximately centered on the sternal midline 16 (or immediately to either side of the sternum 13). The distal end of the electrode patch 15, under which a lower or inferior pole (ECG electrode) is adhered, extends towards the Xiphoid process and lower sternum and, depending upon the patient's build, may straddle the region over the Xiphoid process and lower sternum. The proximal end of the electrode patch 15, located under the monitor recorder 14, under which an upper or superior pole (ECG electrode) is adhered, is below the manubrium and, depending upon patient's build, may straddle the region over the manubrium.

During ECG monitoring, the amplitude and strength of action potentials sensed on the body's surface are affected to varying degrees by cardiac, cellular, extracellular, vector of current flow, and physical factors, like obesity, dermatitis, large breasts, and high impedance skin, as can occur in dark-skinned individuals. Sensing along the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity by countering some of the effects of these factors.

Figure 3:
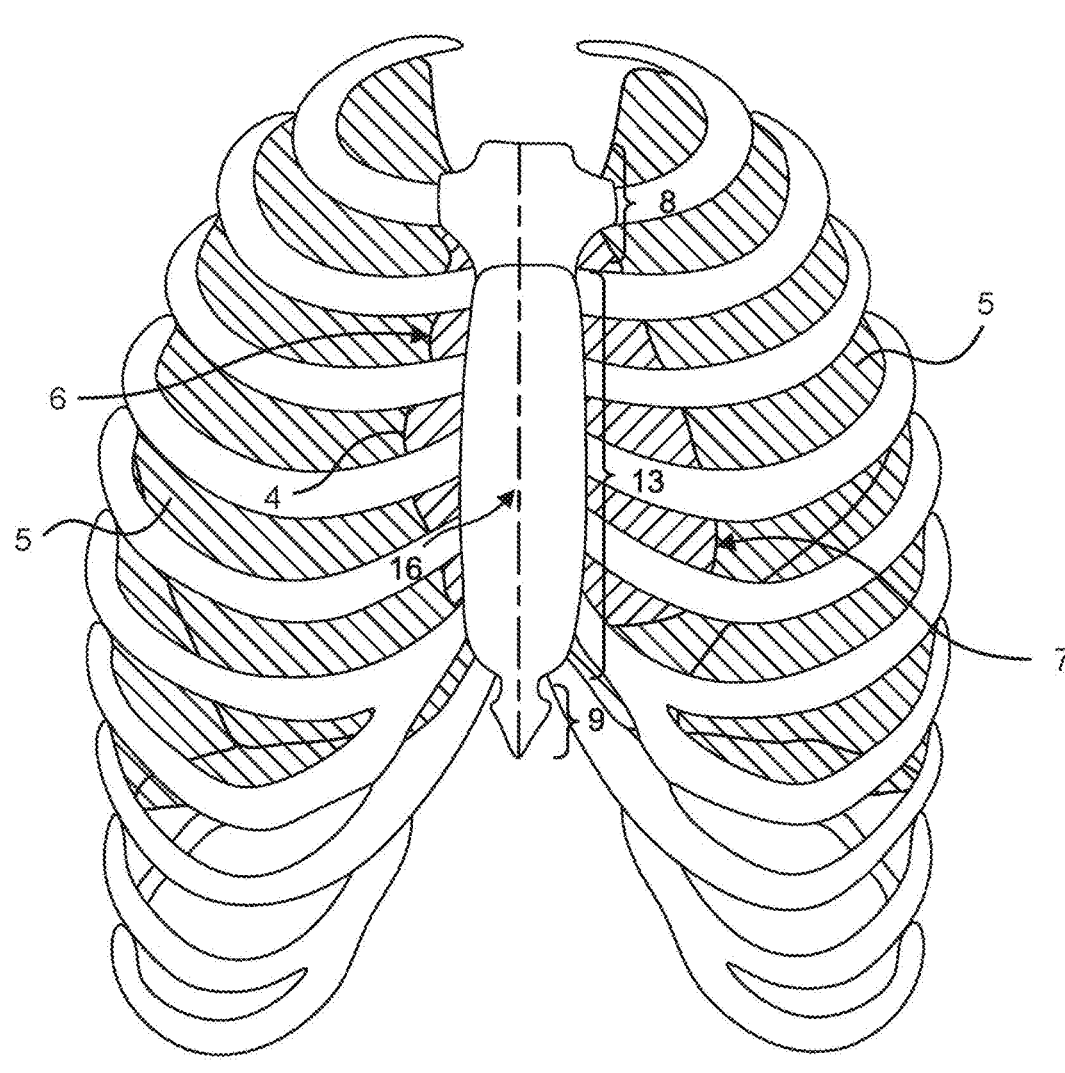
FIG. 3 is a front anatomical view showing, by way of illustration, the locations of the heart and lungs within the rib cage of an adult human.

The ability to sense low amplitude, low frequency content body surface potentials is directly related to the location of ECG electrodes on the skin's surface and the ability of the sensing circuitry to capture these electrical signals. FIG. 3 is a front anatomical view showing, by way of illustration, the locations of the heart 4 and lungs 5 within the rib cage of an adult human. Depending upon their placement locations on the chest, ECG electrodes may be separated from activation regions within the heart 4 by differing combinations of internal tissues and body structures, including heart muscle, intracardiac blood, the pericardium, intrathoracic blood and fluids, the lungs 5, skeletal muscle, bone structure, subcutaneous fat, and the skin, plus any contaminants present between the skin's surface and electrode signal pickups. The degree of amplitude degradation of cardiac transmembrane potentials increases with the number of tissue boundaries between the heart 4 and the skin's surface that are encountered. The cardiac electrical field is degraded each time the transmembrane potentials encounter a physical boundary separating adjoining tissues due to differences in the respective tissues' electrical resistances. In addition, other non-spatial factors, such as pericardial effusion, emphysema or fluid accumulation in the lungs, as further explained infra, can further degrade body surface potentials.

Internal tissues and body structures can adversely affect the current strength and signal fidelity of all body surface potentials, yet low amplitude cardiac action potentials, particularly the P-wave with a normative amplitude of less than 0.25 microvolts (mV) and a normative duration of less than 120 milliseconds (ms), are most apt to be negatively impacted. The atria 6 are generally located posteriorly within the thoracic cavity (with the exception of the anterior right atrium and right atrial appendage), and, physically, the left atrium constitutes the portion of the heart 4 furthest away from the surface of the skin on the chest. Conversely, the ventricles 7, which generate larger amplitude signals, generally are located anteriorly with the anterior right ventricle and most of the left ventricle situated relatively close to the skin surface on the chest, which contributes to the relatively stronger amplitudes of ventricular waveforms. Thus, the quality of P-waves (and other already-low amplitude action potential signals) is more susceptible to weakening from intervening tissues and structures than the waveforms associated with ventricular activation.

The importance of the positioning of ECG electrodes along the sternal midline 15 has largely been overlooked by conventional approaches to ECG monitoring, in part due to the inability of their sensing circuitry to reliably detect low amplitude, low frequency content electrical signals, particularly in P-waves. In turn, that inability to keenly sense P-waves has motivated ECG electrode placement in other non-sternal midline thoracic locations, where the QRSTU components that represent ventricular electrical activity are more readily detectable by their sensing circuitry than P-waves. In addition, ECG electrode placement along the sternal midline 15 presents major patient wearability challenges, such as fitting a monitoring ensemble within the narrow confines of the inter-mammary cleft between the breasts, that to large extent drive physical packaging concerns, which can be incompatible with ECG monitors intended for placement, say, in the upper pectoral region or other non-sternal midline thoracic locations. In contrast, the wearable monitor 12 uses an electrode patch 15 that is specifically intended for extended wear placement in a location at the sternal midline 16 (or immediately to either side of the sternum 13). When combined with a monitor recorder 14 that uses sensing circuitry optimized to preserve the characteristics of low amplitude cardiac action potentials, especially those signals from the atria, as further described infra with reference to FIG. 11, the electrode patch 15 helps to significantly improve atrial activation (P-wave) sensing through placement in a body location that robustly minimizes the effects of tissue and body structure.

Referring back to FIGS. 1 and 2, the placement of the wearable monitor 12 in the region of the sternal midline 13 puts the ECG electrodes of the electrode patch 15 in locations better adapted to sensing and recording low amplitude cardiac action potentials during atrial propagation (P-wave signals) than placement in other locations, such as the upper left pectoral region, as commonly seen in most conventional ambulatory ECG monitors. The sternum 13 overlies the right atrium of the heart 4. As a result, action potential signals have to travel through fewer layers of tissue and structure to reach the ECG electrodes of the electrode patch 15 on the body's surface along the sternal midline 13 when compared to other monitoring locations, a distinction that is of critical importance when capturing low frequency content electrical signals, such as P-waves.

Moreover, cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the AV node. The ECG electrodes of the electrode patch 15 are placed with the upper or superior pole (ECG electrode) along the sternal midline 13 in the region of the manubrium and the lower or inferior pole (ECG electrode) along the sternal midline 13 in the region of the Xiphoid process 9 and lower sternum. The ECG electrodes are placed primarily in a north-to-south orientation along the sternum 13 that corresponds to the north-to-south waveform vector exhibited during atrial activation. This orientation corresponds to the aVF lead used in a conventional 12-lead ECG that is used to sense positive or upright P-waves.

Furthermore, the thoracic region underlying the sternum 13 along the midline 16 between the manubrium 8 and Xiphoid process 9 is relatively free of lung tissue, musculature, and other internal body structures that could occlude the electrical signal path between the heart 4, particularly the atria, and ECG electrodes placed on the surface of the skin. Fewer obstructions means that cardiac electrical potentials encounter fewer boundaries between different tissues. As a result, when compared to other thoracic ECG sensing locations, the cardiac electrical field is less altered when sensed dermally along the sternal midline 13. As well, the proximity of the sternal midline 16 to the ventricles 7 facilitates sensing of right ventricular activity and provides superior recordation of the QRS interval, again, in part due to the relatively clear electrical path between the heart 4 and the skin surface.

Finally, non-spatial factors can affect transmembrane action potential shape and conductivity. For instance, myocardial ischemia, an acute cardiac condition, can cause a transient increase in blood perfusion in the lungs 5. The perfused blood can significantly increase electrical resistance across the lungs 5 and therefore degrade transmission of the cardiac electrical field to the skin's surface. However, the placement of the wearable monitor 12 along the sternal midline 16 in the inter-mammary cleft between the breasts is relatively resilient to the adverse effects to cardiac action potential degradation caused by ischemic conditions as the body surface potentials from a location relatively clear of underlying lung tissue and fat help compensate for the loss of signal amplitude and content. The monitor recorder 14 is thus able to record the P-wave morphology that may be compromised by myocardial ischemia and therefore make diagnosis of the specific arrhythmias that can be associated with myocardial ischemia more difficult.

Figure 4:
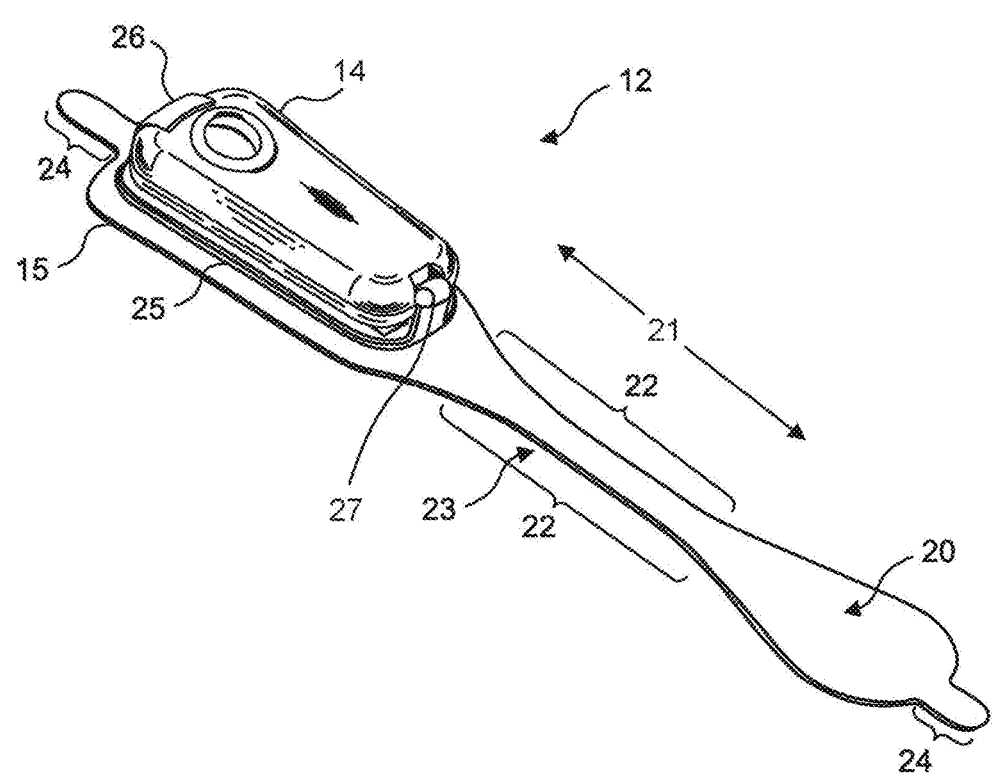
FIG. 4 is a perspective view showing an extended wear electrode patch in accordance with one embodiment with a monitor recorder inserted.

During use, the electrode patch 15 is first adhered to the skin along the sternal midline 16 (or immediately to either side of the sternum 13). A monitor recorder 14 is then snapped into place on the electrode patch 15 using an electro mechanical docking interface to initiate ECG monitoring. FIG. 4 is a perspective view showing an extended wear electrode patch 15 in accordance with one embodiment with a monitor recorder 14 inserted. The body of the electrode patch 15 is preferably constructed using a flexible backing 20 formed as an elongated strip 21 of wrap knit or similar stretchable material about 145 mm long and 32 mm at the widest point with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above, such as described in commonly-assigned U.S. Design Pat. No. D744,659, issued Dec. 1, 2015, the disclosure of which is incorporated by reference. The upper part of the "hourglass" is sized to allow an electrically non-conductive receptacle 25, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile (but still rounded and tapered to fit comfortably between the breasts) than the lower part of the "hourglass," which is sized primarily to allow just the placement of an ECG electrode of appropriate shape and surface area to record the P-wave and the QRS signals sufficiently given the inter-electrode spacing.

The electrode patch 15 incorporates features that significantly improve wearability, performance, and patient comfort throughout an extended monitoring period. The entire electrode patch 15 is lightweight in construction, which allows the patch to be resilient to disadhesing or falling off and, critically, to avoid creating distracting discomfort to the patient, even when the patient is asleep. In contrast, the weight of a heavy ECG monitor impedes patient mobility and will cause the monitor to constantly tug downwards and press on the patient's body that can generate skin inflammation with frequent adjustments by the patient needed to maintain comfort.

During every day wear, the electrode patch 15 is subjected to pushing, pulling, and torsional movements, including compressional and torsional forces when the patient bends forward, or tensile and torsional forces when the patient leans backwards. To counter these stress forces, the electrode patch 15 incorporates crimp and strain reliefs, such as described in commonly-assigned U.S. Pat. No. 9,545,204, issued Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the inter-mammary cleft between the breasts, especially in buxom women. The cut-outs 22 and narrow and flexible longitudinal midsection 23 help the electrode patch 15 fit nicely between a pair of female breasts in the inter-mammary cleft. In one embodiment, the cut-outs 22 can be graduated to form the longitudinal midsection 23 as a narrow in-between stem or isthmus portion about 7 mm wide. In a still further embodiment, tabs 24 can respectively extend an additional 8 mm to 12 mm beyond the distal and proximal ends of the flexible backing 20 to facilitate with adhering the electrode patch 15 to or removing the electrode patch 15 from the sternum 13. These tabs preferably lack adhesive on the underside, or contact, surface of the electrode patch 15. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, as further described infra beginning with reference to FIG. 9. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
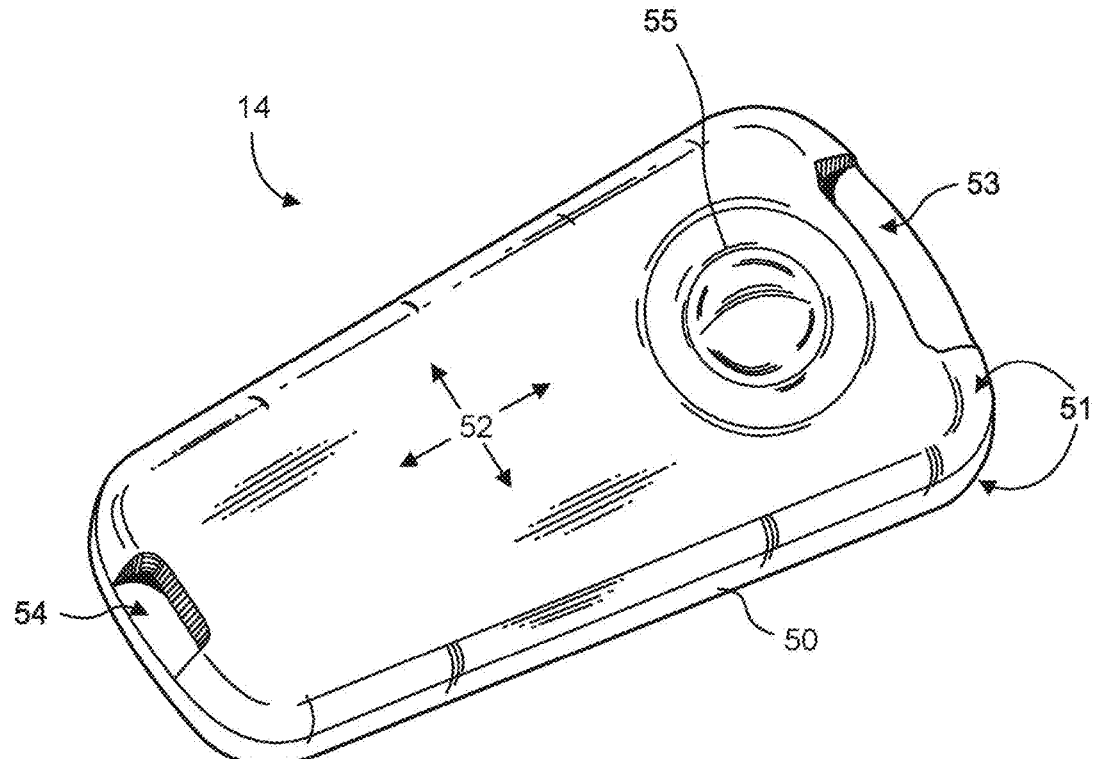
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Pat. No. D717,955, issued Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable, while the monitor recorder 14 is designed for reuse and can be transferred to successive electrode patches 15 to ensure continuity of monitoring, if so desired. The monitor recorder 14 can be used only once, but single use effectively wastes the synergistic benefits provided by the combination of the disposable electrode patch and reusable monitor recorder, as further explained infra with reference to FIGS. 16A-C. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
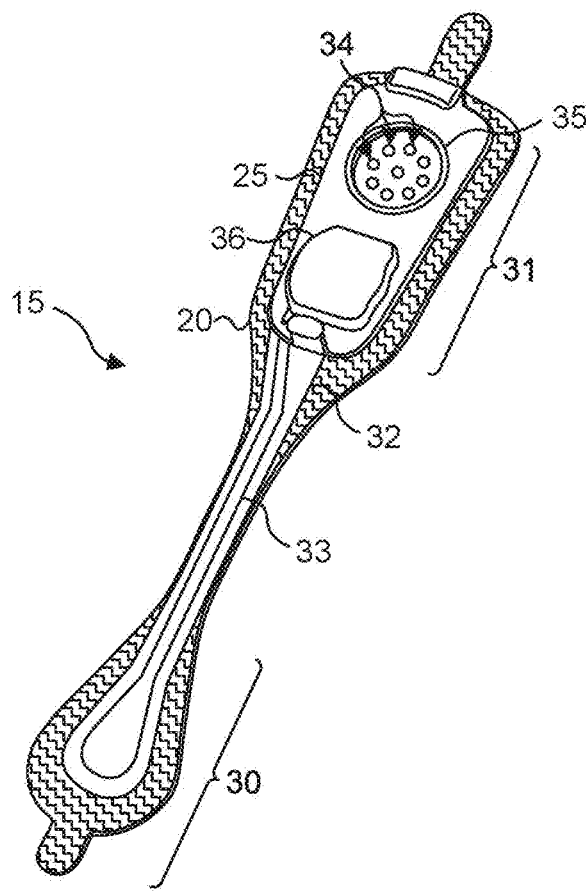
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 from the distal end 30 of the flexible backing 20 and a proximal circuit trace (not shown) from the proximal end 31 of the flexible backing 20 electrically couple ECG electrodes (not shown) with a pair of electrical pads 34. In a further embodiment, the distal and proximal circuit traces are replaced with interlaced or sewn-in flexible wires, as further described infra beginning with reference to FIG. 17. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14. The moisture-resistant seal 35 enables the monitor recorder 14 to be worn at all times, even during showering or other activities that could expose the monitor recorder 14 to moisture or adverse conditions.

In addition, a battery compartment 36 is formed on the bottom surface of the non-conductive receptacle 25. A pair of battery leads (not shown) from the battery compartment 36 to another pair of the electrical pads 34 electrically interface the battery to the monitor recorder 14. The battery contained within the battery compartment 35 is a direct current (DC) power cell and can be replaceable, rechargeable or disposable.

Figure 7:
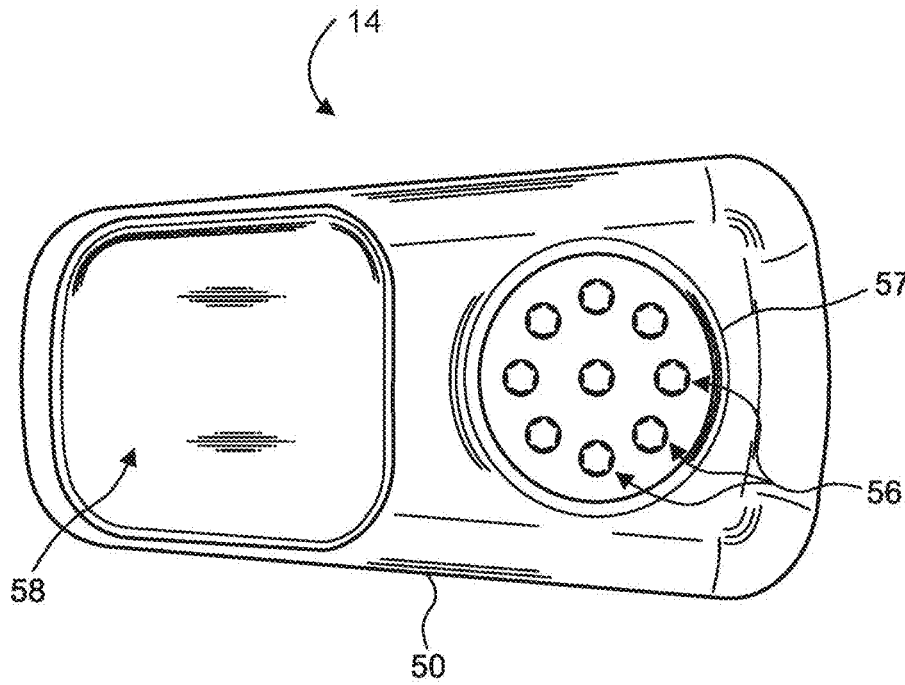
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25. The battery contained within the battery compartment 36 can be replaceable, rechargeable or disposable. In a further embodiment, the ECG sensing circuitry of the monitor recorder 14 can be supplemented with additional sensors, including an $SpO_2$ sensor, a blood pressure sensor, a temperature sensor, respiratory rate sensor, a glucose sensor, an air flow sensor, and a volumetric pressure sensor, which can be incorporated directly into the monitor recorder 14 or onto the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. However, the wearable monitor 12 is still susceptible to pushing, pulling, and torqueing movements, including compressional and torsional forces when the patient bends forward, and tensile and torsional forces when the patient leans backwards or twists. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 8:
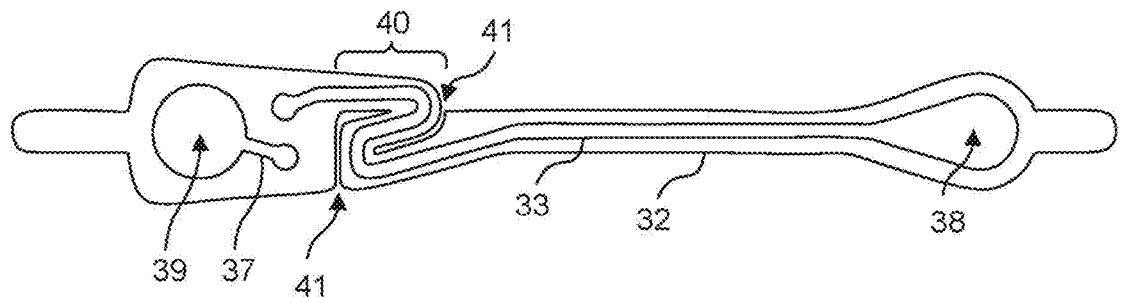
FIG. 8 is a top view showing the flexible circuit of the extended wear electrode patch of FIG. 4.

Unlike the flexible backing 20, the flexible circuit 32 is only able to bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32 to serve as electrode signal pickups. The flexible circuit 32 preferably does not extend to the outside edges of the flexible backing 20, thereby avoiding gouging or discomforting the patient's skin during extended wear, such as when sleeping on the side. During wear, the ECG electrodes 38, 39 must remain in continual contact with the skin. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to bending, tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 9:
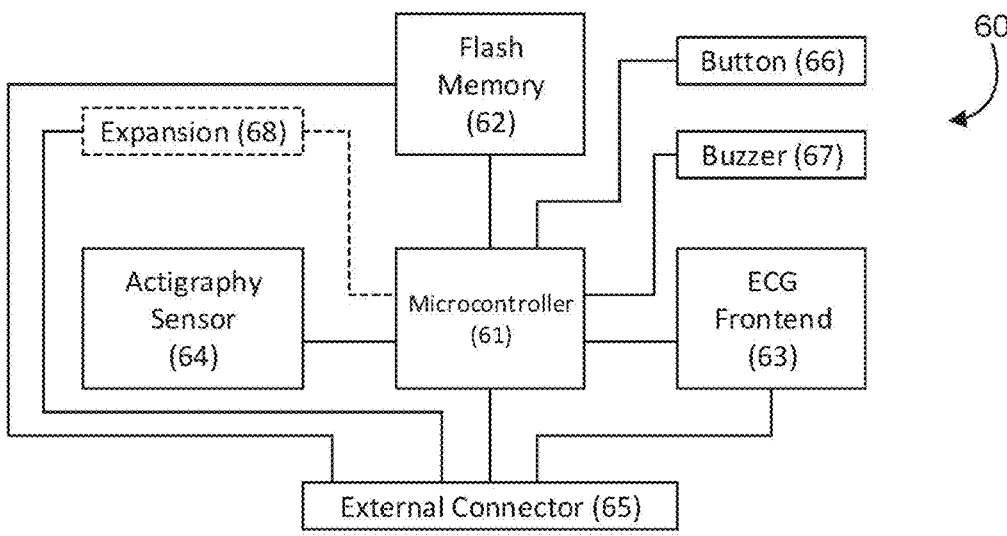
FIG. 9 is a functional block diagram showing the component architecture of the circuitry of the monitor recorder of FIG. 4.

ECG monitoring and other functions performed by the monitor recorder 14 are provided through a micro controlled architecture. FIG. 9 is a functional block diagram showing the component architecture of the circuitry 60 of the monitor recorder 14 of FIG. 4. The circuitry 60 is externally powered through a battery provided in the non-conductive receptacle 25 (shown in FIG. 6). Both power and raw ECG signals, which originate in the pair of ECG electrodes 38, 39 (shown in FIG. 8) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions. The download station is further described infra with reference to FIG. 15.

Operation of the circuitry 60 of the monitor recorder 14 is managed by a microcontroller 61, such as the EFM32 Tiny Gecko 32-bit microcontroller, manufactured by Silicon Laboratories Inc., Austin, TX. The microcontroller 61 has flexible energy management modes and includes a direct memory access controller and built-in analog-to-digital and digital-to-analog converters (ADC and DAC, respectively). The microcontroller 61 also includes a program memory unit containing internal flash memory that is readable and writeable. The internal flash memory can also be programmed externally. The microcontroller 61 operates under modular micro program control as specified in firmware stored in the internal flash memory. The functionality and firmware modules relating to signal processing by the microcontroller 61 are further described infra with reference to FIG. 14. The microcontroller 61 draws power externally from the battery provided on the electrode patch 15 via a pair of the electrical contacts 56. The microcontroller 61 connects to the ECG front end circuit 63 that measures raw cutaneous electrical signals using a driven reference that eliminates common mode noise, as further described infra with reference to FIG. 11.

The circuitry 60 of the monitor recorder 14 also includes a flash memory 62, which the microcontroller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

Figure 14:
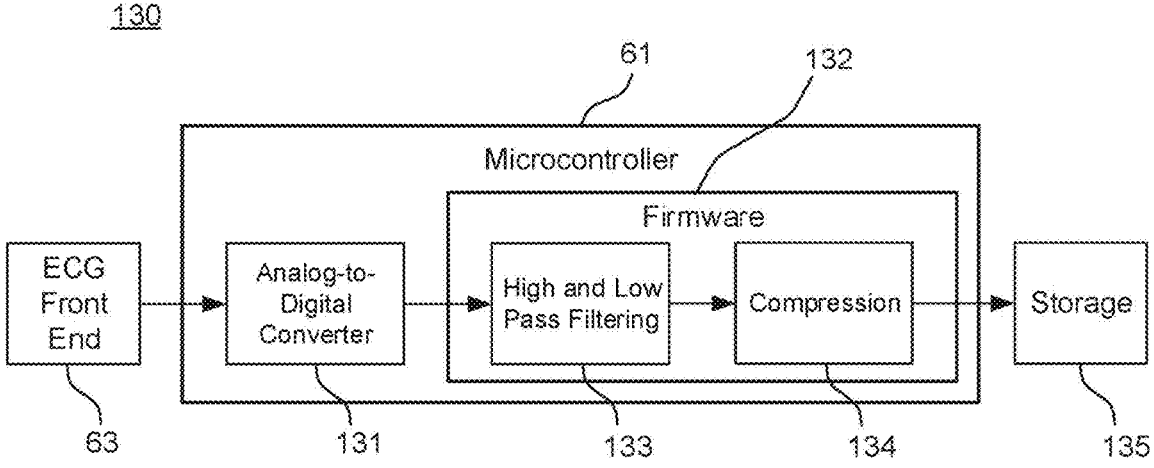
FIG. 14 is a functional block diagram showing the signal processing functionality of the microcontroller.

The microcontroller 61 includes functionality that enables the acquisition of samples of analog ECG signals, which are converted into a digital representation, as further described infra with reference to FIG. 14. In one mode, the microcontroller 61 will acquire, sample, digitize, signal process, and store digitized ECG data into available storage locations in the flash memory 62 until all memory storage locations are filled, after which the digitized ECG data needs to be downloaded or erased to restore memory capacity. Data download or erasure can also occur before all storage locations are filled, which would free up memory space sooner, albeit at the cost of possibly interrupting monitoring while downloading or erasure is performed. In another mode, the microcontroller 61 can include a loop recorder feature that will overwrite the oldest stored data once all storage locations are filled, albeit at the cost of potentially losing the stored data that was overwritten, if not previously downloaded. Still other modes of data storage and capacity recovery are possible.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the microcontroller 61 provided over one of the electrical contacts 56. The physiology sensor can include an SpO$_2$ sensor, blood pressure sensor, temperature sensor, respiratory rate sensor, glucose sensor, airflow sensor, volumetric pressure sensing, or other types of sensor or telemetric input sources. In a further embodiment, a wireless interface for interfacing with other wearable (or implantable) physiology monitors, as well as data offload and programming, can be provided as part of the circuitry 60 of the monitor recorder 14, or can be provided on the electrode patch 15 with communication with the microcontroller 61 provided over one of the electrical contacts 56.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

Figure 10:
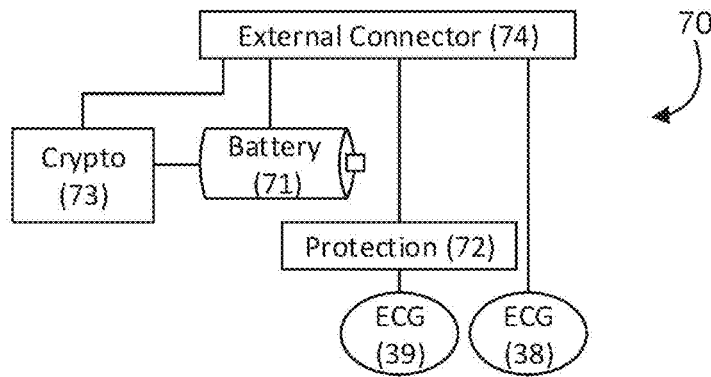
FIG. 10 is a functional block diagram showing the circuitry of the extended wear electrode patch of FIG. 4.

While the monitor recorder 14 operates under micro control, most of the electrical components of the electrode patch 15 operate passively. FIG. 10 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Also, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. This approach also enables a battery of higher capacity to be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current should the front end circuit fail.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14 and for a specific patient.

Figure 11:
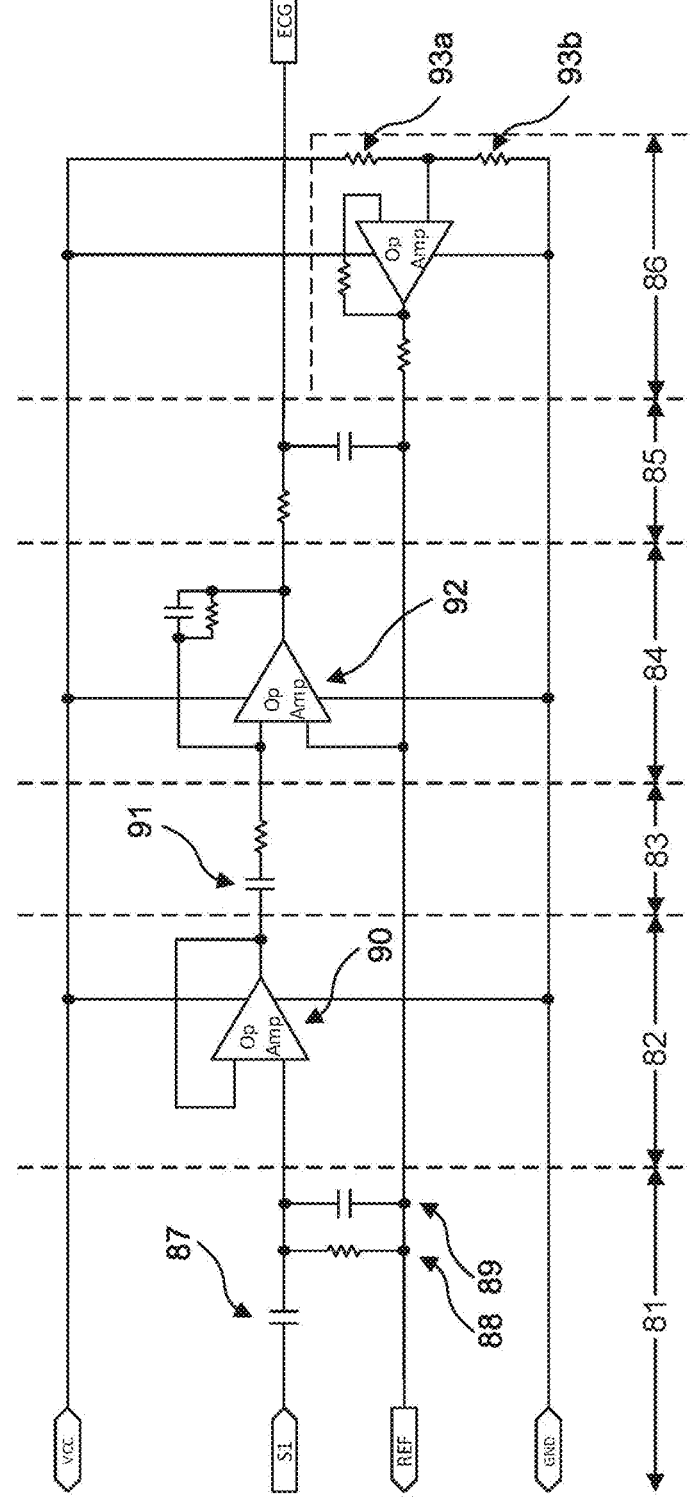
FIG. 11 is a schematic diagram showing the ECG front end circuit of the circuitry of the monitor recorder of FIG. 9.

The ECG front end circuit 63 measures raw cutaneous electrical signals using a driven reference that effectively reduces common mode noise, power supply noise and system noise, which is critical to preserving the characteristics of low amplitude cardiac action potentials, especially those signals from the atria. FIG. 11 is a schematic diagram 80 showing the ECG front end circuit 63 of the circuitry 60 of the monitor recorder 14 of FIG. 9. The ECG front end circuit 63 senses body surface potentials through a signal lead ("S1") and reference lead ("REF") that are respectively connected to the ECG electrodes of the electrode patch 15. Power is provided to the ECG front end circuit 63 through a pair of DC power leads ("VCC" and "GND"). An analog ECG signal ("ECG") representative of the electrical activity of the patient's heart over time is output, which the micro controller 11 converts to digital representation and filters, as further described infra.

The ECG front end circuit 63 is organized into five stages, a passive input filter stage 81, a unity gain voltage follower stage 82, a passive high pass filtering stage 83, a voltage amplification and active filtering stage 84, and an anti-aliasing passive filter stage 85, plus a reference generator. Each of these stages and the reference generator will now be described.

The passive input filter stage 81 includes the parasitic impedance of the ECG electrodes 38, 39 (shown in FIG. 8), the protection resistor that is included as part of the protection circuit 72 of the ECG electrode 39 (shown in FIG. 10), an AC coupling capacitor 87, a termination resistor 88, and filter capacitor 89. This stage passively shifts the frequency response poles downward there is a high electrode impedance from the patient on the signal lead S1 and reference lead REF, which reduces high frequency noise.

The unity gain voltage follower stage 82 provides a unity voltage gain that allows current amplification by an Operational Amplifier ("Op Amp") 90. In this stage, the voltage stays the same as the input, but more current is available to feed additional stages. This configuration allows a very high input impedance, so as not to disrupt the body surface potentials or the filtering effect of the previous stage.

The passive high pass filtering stage 83 is a high pass filter that removes baseline wander and any offset generated from the previous stage. Adding an AC coupling capacitor 91 after the Op Amp 90 allows the use of lower cost components, while increasing signal fidelity.

The voltage amplification and active filtering stage 84 amplifies the voltage of the input signal through Op Amp 92, while applying a low pass filter. The DC bias of the input signal is automatically centered in the highest performance input region of the Op Amp 92 because of the AC coupling capacitor 91.

The anti-aliasing passive filter stage 85 provides an anti-aliasing low pass filter. When the microcontroller 61 acquires a sample of the analog input signal, a disruption in the signal occurs as a sample and hold capacitor that is internal to the microcontroller 61 is charged to supply signal for acquisition.

The reference generator in subcircuit 86 drives a driven reference containing power supply noise and system noise to the reference lead REF. A coupling capacitor 87 is included on the signal lead S1 and a pair of resistors 93a, 93b inject system noise into the reference lead REF. The reference generator is connected directly to the patient, thereby avoiding the thermal noise of the protection resistor that is included as part of the protection circuit 72.

In contrast, conventional ECG lead configurations try to balance signal and reference lead connections. The conventional approach suffers from the introduction of differential thermal noise, lower input common mode rejection, increased power supply noise, increased system noise, and differential voltages between the patient reference and the reference used on the device that can obscure, at times, extremely, low amplitude body surface potentials.

Here, the parasitic impedance of the ECG electrodes 38, 39, the protection resistor that is included as part of the protection circuit 72 and the coupling capacitor 87 allow the reference lead REF to be connected directly to the skin's surface without any further components. As a result, the differential thermal noise problem caused by pairing protection resistors to signal and reference leads, as used in conventional approaches, is avoided.

Figure 12:
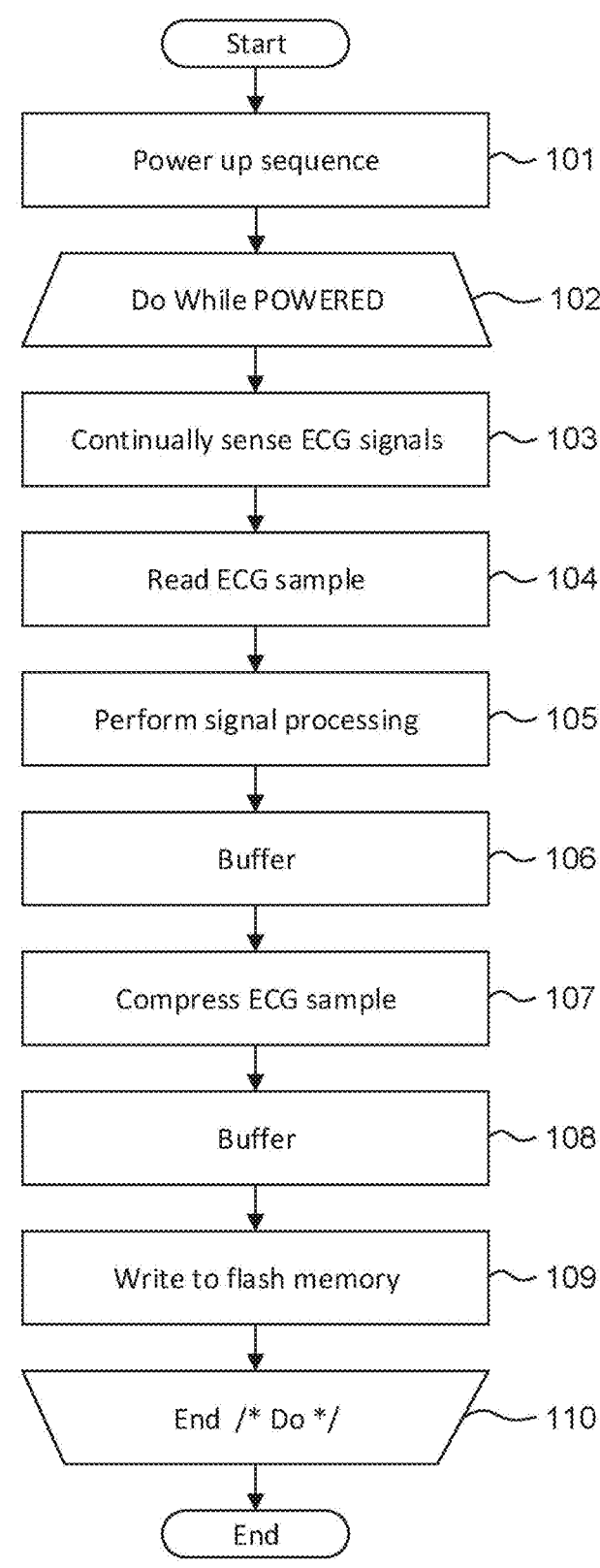
FIG. 12 is a flow diagram showing a monitor recorder-implemented method for monitoring ECG data for use in the monitor recorder of FIG. 4.

The monitor recorder 14 continuously monitors the patient's heart rate and physiology. FIG. 12 is a flow diagram showing a monitor recorder-implemented method 100 for monitoring ECG data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 13:
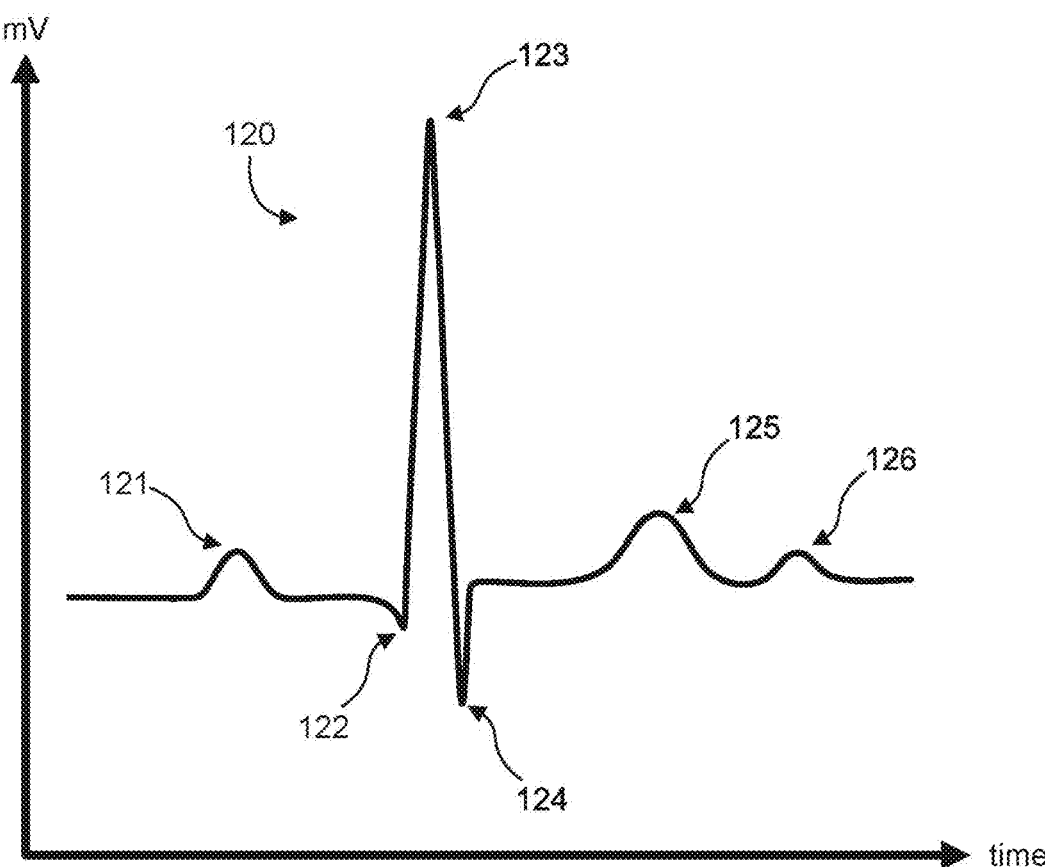
FIG. 13 is a graph showing, by way of example, a typical ECG waveform.

Following satisfactory completion of the power up sequence, an iterative processing loop (steps 102-110) is continually executed by the microcontroller 61. During each iteration (step 102) of the processing loop, the ECG frontend 63 (shown in FIG. 9) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal that is output by the ECG front end circuit 63. FIG. 13 is a graph showing, by way of example, a typical ECG waveform 120. The x-axis represents time in approximate units of tenths of a second. The y-axis represents cutaneous electrical signal strength in approximate units of millivolts. The P-wave 121 has a smooth, normally upward, that is, positive, waveform that indicates atrial depolarization. The QRS complex often begins with the downward deflection of a Q-wave 122, followed by a larger upward deflection of an R-wave 123, and terminated with a downward waveform of the S-wave 124, collectively representative of ventricular depolarization. The T-wave 125 is normally a modest upward waveform, representative of ventricular depolarization, while the U-wave 126, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the ambulatory electrocardiography monitoring patch optimized for capturing low amplitude cardiac action potential propagation described herein is medically unique and important. The long-term observation of these ECG indicia, as provided through extended wear of the wearable monitor 12, provides valuable insights to the patient's cardiac function symptoms, and overall well-being.

Referring back to FIG. 12, each sampled ECG signal, in quantized and digitized form, is processed by signal processing modules as specified in firmware (step 105), as described infra, and temporarily staged in a buffer (step 106), pending compression preparatory to storage in the flash memory 62 (step 107). Following compression, the compressed ECG digitized sample is again buffered (step 108), then written to the flash memory 62 (step 109) using the communications bus. Processing continues (step 110), so long as the monitoring recorder 14 remains connected to the electrode patch 15 (and storage space remains available in the flash memory 62), after which the processing loop is exited (step 110) and execution terminates. Still other operations and steps are possible.

The microcontroller 61 operates under modular micro program control as specified in firmware, and the program control includes processing of the analog ECG signal output by the ECG front end circuit 63. FIG. 14 is a functional block diagram showing the signal processing functionality 130 of the microcontroller 61. The microcontroller 61 operates under modular micro program control as specified in firmware 132. The firmware modules 132 include high and low pass filtering 133, and compression 134. Other modules are possible. The microcontroller 61 has a built-in ADC, although ADC functionality could also be provided in the firmware 132.

The ECG front end circuit 63 first outputs an analog ECG signal, which the ADC 131 acquires, samples and converts into an uncompressed digital representation. The microcontroller 61 includes one or more firmware modules 133 that perform filtering. In one embodiment, three low pass filters and two high pass filters are used. Following filtering, the digital representation of the cardiac activation wave front amplitudes are compressed by a compression module 134 before being written out to storage 135.

Figure 15:
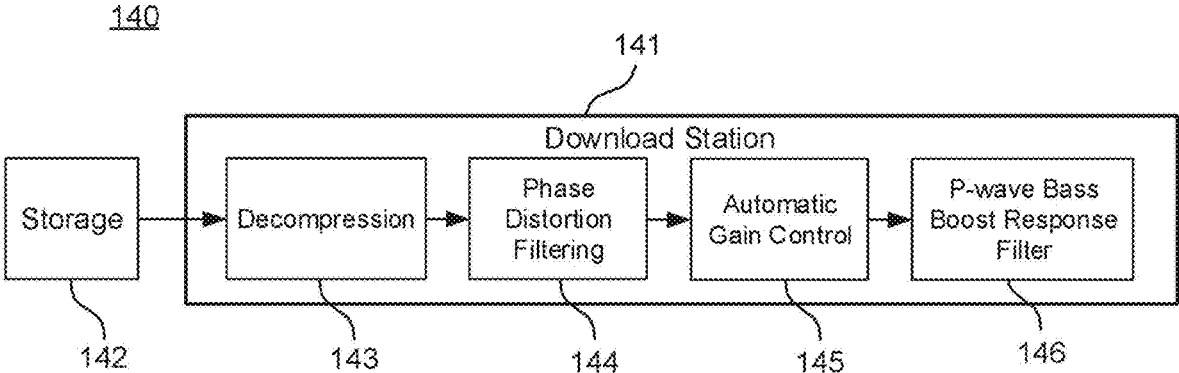
FIG. 15 is a functional block diagram showing the operations performed by the download station.

The download station executes a communications or offload program ("Offload") or similar program that interacts with the monitor recorder 14 via the external connector 65 to retrieve the stored ECG monitoring data. FIG. 15 is a functional block diagram showing the operations 140 performed by the download station. The download station could be a server, personal computer, tablet or handheld computer, smart mobile device, or purpose-built programmer designed specific to the task of interfacing with a monitor recorder 14. Still other forms of download station are possible, including download stations connected through wireless interfacing using, for instance, a smart phone connected to the monitor recorder 14 through Bluetooth or Wi-Fi.

The download station is responsible for offloading stored ECG monitoring data from a monitor recorder 14 and includes an electro mechanical docking interface by which the monitor recorder 14 is connected at the external connector 65. The download station operates under programmable control as specified in software 141. The stored ECG monitoring data retrieved from storage 142 on a monitor recorder 14 is first decompressed by a decompression module 143, which converts the stored ECG monitoring data back into an uncompressed digital representation more suited to signal processing than a compressed signal. The retrieved ECG monitoring data may be stored into local storage for archival purposes, either in original compressed form, or as uncompressed.

The download station can include an array of filtering modules. For instance, a set of phase distortion filtering tools 144 may be provided, where corresponding software filters can be provided for each filter implemented in the firmware executed by the microcontroller 61. The digital signals are run through the software filters in a reverse direction to remove phase distortion. For instance, a 45 Hertz high pass filter in firmware may have a matching reverse 45 Hertz high pass filter in software. Most of the phase distortion is corrected, that is, canceled to eliminate noise at the set frequency, but data at other frequencies in the waveform remain unaltered. As well, bidirectional impulse infinite response (IIR) high pass filters and reverse direction (symmetric) IIR low pass filters can be provided. Data is run through these filters first in a forward direction, then in a reverse direction, which generates a square of the response and cancels out any phase distortion. This type of signal processing is particularly helpful with improving the display of the ST-segment by removing low frequency noise.

An automatic gain control (AGC) module 145 can also be provided to adjust the digital signals to a usable level based on peak or average signal level or other metric. AGC is particularly critical to single-lead ECG monitors, where physical factors, such as the tilt of the heart, can affect the electrical field generated. On three-lead Holter monitors, the leads are oriented in vertical, horizontal and diagonal directions. As a result, the horizontal and diagonal leads may be higher amplitude and ECG interpretation will be based on one or both of the higher amplitude leads. In contrast, the electrocardiography monitor 12 has only a single lead that is oriented in the vertical direction, so variations in amplitude will be wider than available with multi-lead monitors, which have alternate leads to fall back upon.

In addition, AGC may be necessary to maintain compatibility with existing ECG interpretation software, which is typically calibrated for multi-lead ECG monitors for viewing signals over a narrow range of amplitudes. Through the AGC module 145, the gain of signals recorded by the monitor recorder 14 of the electrocardiography monitor 12 can be attenuated up (or down) to work with FDA-approved commercially available ECG interpretation.

AGC can be implemented in a fixed fashion that is uniformly applied to all signals in an ECG recording, adjusted as appropriate on a recording-by-recording basis. Typically, a fixed AGC value is calculated based on how an ECG recording is received to preserve the amplitude relationship between the signals. Alternatively, AGC can be varied dynamically throughout an ECG recording, where signals in different segments of an ECG recording are amplified up (or down) by differing amounts of gain.

Typically, the monitor recorder 14 will record a high resolution, low frequency signal for the P-wave segment. However, for some patients, the result may still be a visually small signal. Although high resolution is present, the unaided eye will normally be unable to discern the P-wave segment. Therefore, gaining the signal is critical to visually depicting P-wave detail. This technique works most efficaciously with a raw signal with low noise and high resolution, as generated by the monitor recorder 14. Automatic gain control applied to a high noise signal will only exacerbate noise content and be self-defeating.

Finally, the download station can include filtering modules specifically intended to enhance P-wave content. For instance, a P-wave base boost filter 146, which is a form of pre-emphasis filter, can be applied to the signal to restore missing frequency content or to correct phase distortion. Still other filters and types of signal processing are possible.

Figure 16A:
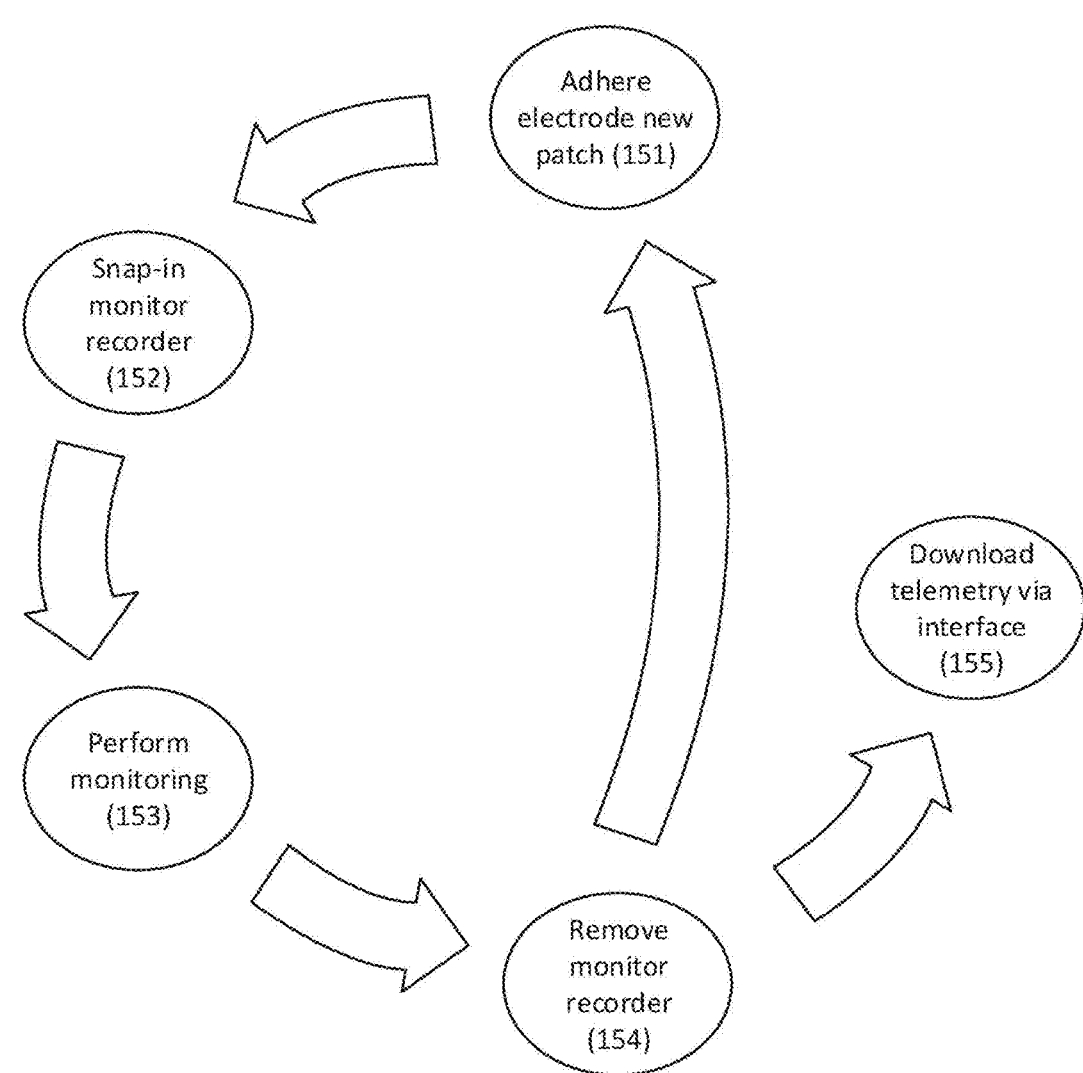
FIGS. 16A-C are functional block diagrams respectively showing practical uses of the extended wear electrocardiography monitors of FIGS. 1 and 2.
Figure 16B:
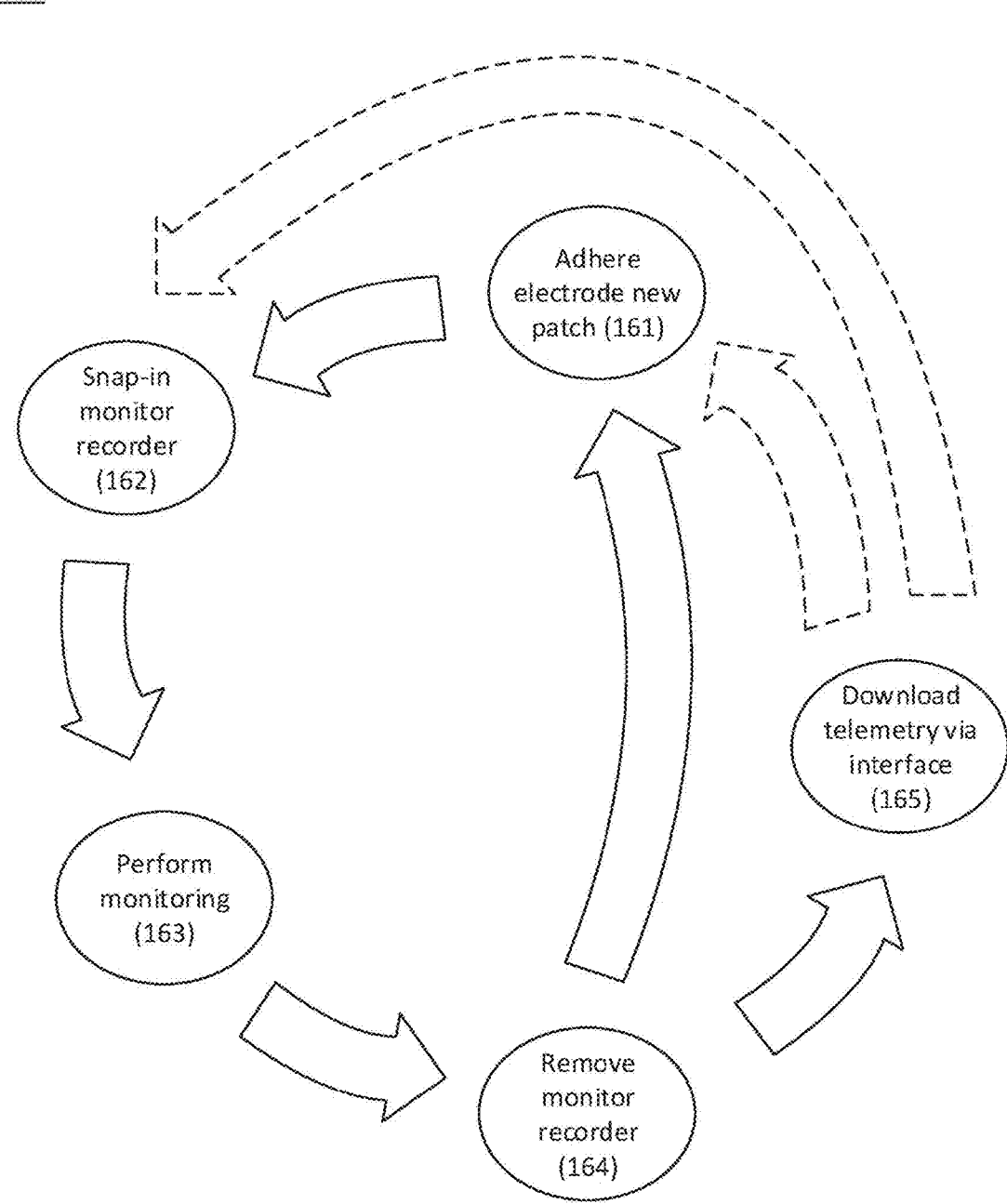
Figure 16C:
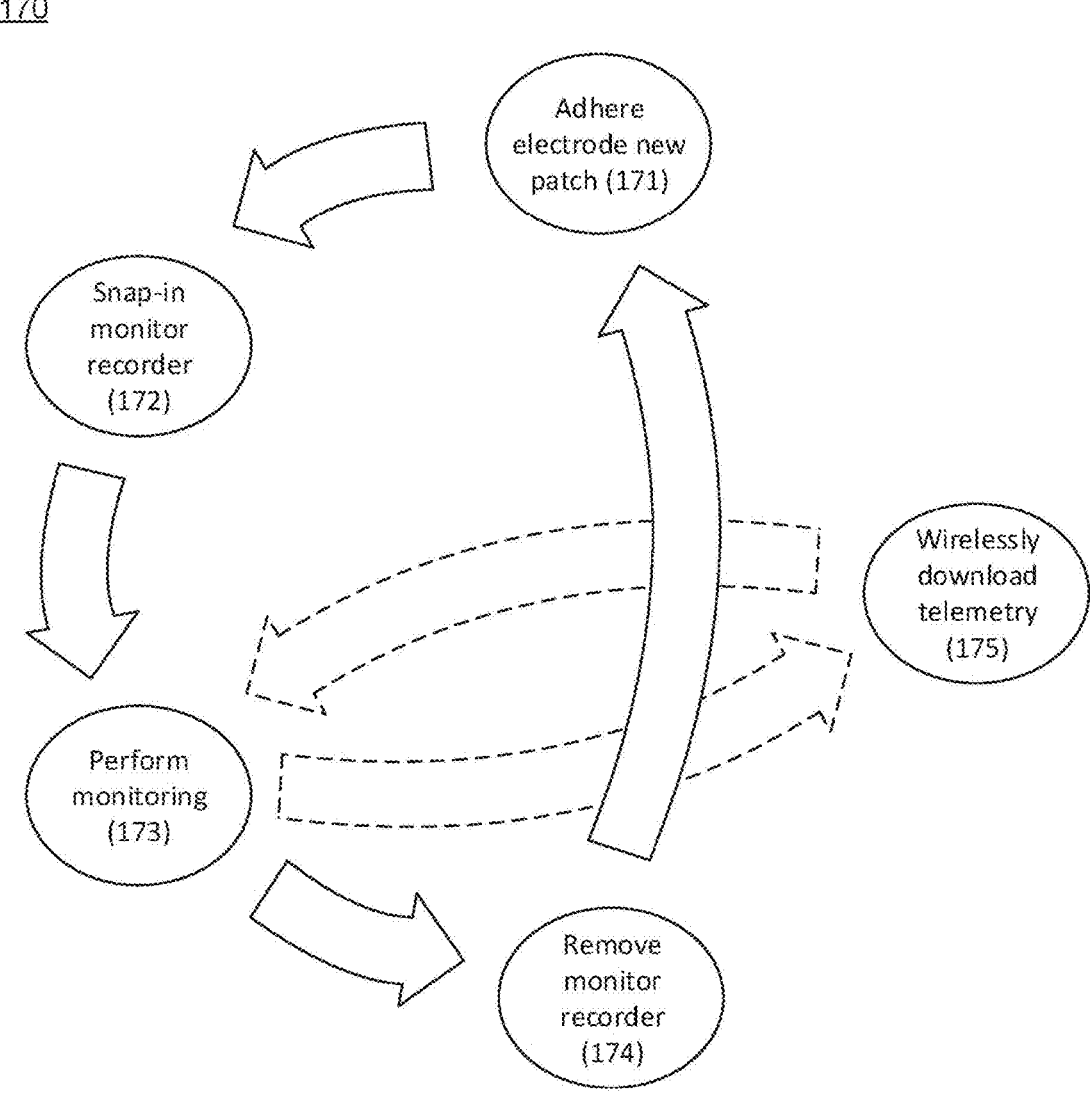

Conventional ECG monitors, like Holter monitors, invariably require specialized training on proper placement of leads and on the operation of recording apparatuses, plus support equipment purpose-built to retrieve, convert, and store ECG monitoring data. In contrast, the electrocardiography monitor 12 simplifies monitoring from end to end, starting with placement, then with use, and finally with data retrieval. FIGS. 16A-C are functional block diagrams respectively showing practical uses 150, 160, 170 of the extended wear electrocardiography monitors 12 of FIGS. 1 and 2. The combination of a flexible extended wear electrode patch and a removable reusable (or single use) monitor recorder empowers physicians and patients alike with the ability to readily perform long-term ambulatory monitoring of the ECG and physiology.

Especially when compared to existing Holter-type monitors and monitoring patches placed in the upper pectoral region, the electrocardiography monitor 12 offers superior patient comfort, convenience and user-friendliness. To start, the electrode patch 15 is specifically designed for ease of use by a patient (or caregiver); assistance by professional medical personnel is not required. Moreover, the patient is free to replace the electrode patch 15 at any time and need not wait for a doctor's appointment to have a new electrode patch 15 placed. In addition, the monitor recorder 14 operates automatically and the patient only need snap the monitor recorder 14 into place on the electrode patch 15 to initiate ECG monitoring. Thus, the synergistic combination of the electrode patch 15 and monitor recorder 14 makes the use of the electrocardiography monitor 12 a reliable and virtually foolproof way to monitor a patient's ECG and physiology for an extended, or even open-ended, period of time.

In simplest form, extended wear monitoring can be performed by using the same monitor recorder 14 inserted into a succession of fresh new electrode patches 15. As needed, the electrode patch 15 can be replaced by the patient (or caregiver) with a fresh new electrode patch 15 throughout the overall monitoring period. Referring first to FIG. 16A, at the outset of monitoring, a patient adheres a new electrode patch 15 in a location at the sternal midline 16 (or immediately to either side of the sternum 13) oriented top-to-bottom (step 151). The placement of the wearable monitor in a location at the sternal midline (or immediately to either side of the sternum), with its unique narrow "hourglass"-like shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms.

Placement involves simply adhering the electrode patch 15 on the skin along the sternal midline 16 (or immediately to either side of the sternum 13). Patients can easily be taught to find the physical landmarks on the body necessary for proper placement of the electrode patch 15. The physical landmarks are locations on the surface of the body that are already familiar to patients, including the inter-mammary cleft between the breasts above the manubrium (particularly easily locatable by women and gynecomastic men), the sternal notch immediately above the manubrium, and the Xiphoid process located at the bottom of the sternum. Empowering patients with the knowledge to place the electrode patch 15 in the right place ensures that the ECG electrodes will be correctly positioned on the skin, no matter the number of times that the electrode patch 15 is replaced.

A monitor recorder 14 is snapped into the non-conductive receptacle 25 on the outward-facing surface of the electrode patch 15 (step 152). The monitor recorder 14 draws power externally from a battery provided in the non-conductive receptacle 25. In addition, the battery is replaced each time that a fresh new electrode patch 15 is placed on the skin, which ensures that the monitor recorder 14 is always operating with a fresh power supply and minimizing the chances of a loss of monitoring continuity due to a depleted battery source.

By default, the monitor recorder 14 automatically initiates monitoring upon sensing body surface potentials through the pair of ECG electrodes (step 153). In a further embodiment, the monitor recorder 14 can be configured for manual operation, such as by using the tactile feedback button 66 on the outside of the sealed housing 50, or other user-operable control. In an even further embodiment, the monitor recorder 14 can be configured for remotely-controlled operation by equipping the monitor recorder 14 with a wireless transceiver, such as described in commonly-assigned U.S. Pat. No. 9,433,367, issued Sep. 6, 2016, the disclosure of which is incorporated by reference. The wireless transceiver allows wearable or mobile communications devices to wirelessly interface with the monitor recorder 14.

A key feature of the extended wear electrocardiography monitor 12 is the ability to monitor ECG and physiological data for an extended period of time, which can be well in excess of the 14 days currently pitched as being achievable by conventional ECG monitoring approaches. In a further embodiment, ECG monitoring can even be performed over an open-ended time period, as further explained infra. The monitor recorder 14 is reusable and, if so desired, can be transferred to successive electrode patches 15 to ensure continuity of monitoring. At any point during ECG monitoring, a patient (or caregiver) can remove the monitor recorder 14 (step 154) and replace the electrode patch 15 currently being worn with a fresh new electrode patch 15 (step 151). The electrode patch 15 may need to be replaced for any number of reasons. For instance, the electrode patch 15 may be starting to come off after a period of wear or the patient may have skin that is susceptible to itching or irritation. The wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose.

Following replacement, the monitor recorder 14 is again snapped into the electrode patch 15 (step 152) and monitoring resumes (step 153). The ability to transfer the same monitor recorder 14 to successive electrode patches 15 during a period of extended wear monitoring is advantageous not to just diagnose cardiac rhythm disorders and other physiological events of potential concern, but to do extremely long term monitoring, such as following up on cardiac surgery, ablation procedures, or medical device implantation. In these cases, several weeks of monitoring or more may be needed. In addition, some IMDs, such as pacemakers or implantable cardioverter defibrillators, incorporate a loop recorder that will capture cardiac events over a fixed time window. If the telemetry recorded by the IMD is not downloaded in time, cardiac events that occurred at a time preceding the fixed time window will be overwritten by the IMD and therefore lost. The monitor recorder 14 provides continuity of monitoring that acts to prevent loss of cardiac event data. In a further embodiment, the firmware executed by the microcontroller 61 of the monitor recorder 14 can be optimized for minimal power consumption and additional flash memory for storing monitoring data can be added to achieve a multi-week monitor recorder 14 that can be snapped into a fresh new electrode patch 15 every seven days, or other interval, for weeks or even months on end.

Upon the conclusion of monitoring, the monitor recorder 14 is removed (step 154) and recorded ECG and physiological telemetry are downloaded (step 155). For instance, a download station can be physically interfaced to the external connector 65 of the monitor recorder 14 to initiate and conduct downloading, as described supra with reference to FIG. 15.

In a further embodiment, the monitoring period can be of indeterminate duration. Referring next to FIG. 16B, a similar series of operations are followed with respect to replacement of electrode patches 15, reinsertion of the same monitor recorder 14, and eventual download of ECG and physiological telemetry (steps 161-165), as described supra with reference to FIG. 16A. However, the flash memory 62 (shown in FIG. 9) in the circuitry 60 of the monitor recorder 14 has a finite capacity. Following successful downloading of stored data, the flash memory 62 can be cleared to restore storage capacity and monitoring can resume once more, either by first adhering a new electrode patch 15 (step 161) or by snapping the monitor recorder 14 into an already-adhered electrode patch 15 (step 162). The foregoing expanded series of operations, to include reuse of the same monitor recorder 14 following data download, allows monitoring to continue indefinitely and without the kinds of interruptions that often affect conventional approaches, including the retrieval of monitoring data only by first making an appointment with a medical professional.

In a still further embodiment, when the monitor recorder 14 is equipped with a wireless transceiver, the use of a download station can be skipped. Referring last to FIG. 16C, a similar series of operations are followed with respect to replacement of electrode patches 15 and reinsertion of the same monitor recorder 14 (steps 171-174), as described supra with reference to FIG. 16A. However, recorded ECG and physiological telemetry are downloaded wirelessly (step 175), such as described in commonly-assigned U.S. Pat. No. 9,433,367, cited supra. The recorded ECG and physiological telemetry can even be downloaded wirelessly directly from a monitor recorder 14 during monitoring while still snapped into the non-conductive receptacle 25 on the electrode patch 15. The wireless interfacing enables monitoring to continue for an open-ended period of time, as the downloading of the recorded ECG and physiological telemetry will continually free up onboard storage space. Further, wireless interfacing simplifies patient use, as the patient (or caregiver) only need worry about placing (and replacing) electrode patches 15 and inserting the monitor recorder 14. Still other forms of practical use of the extended wear electrocardiography monitors 12 are possible.

Figure 17:
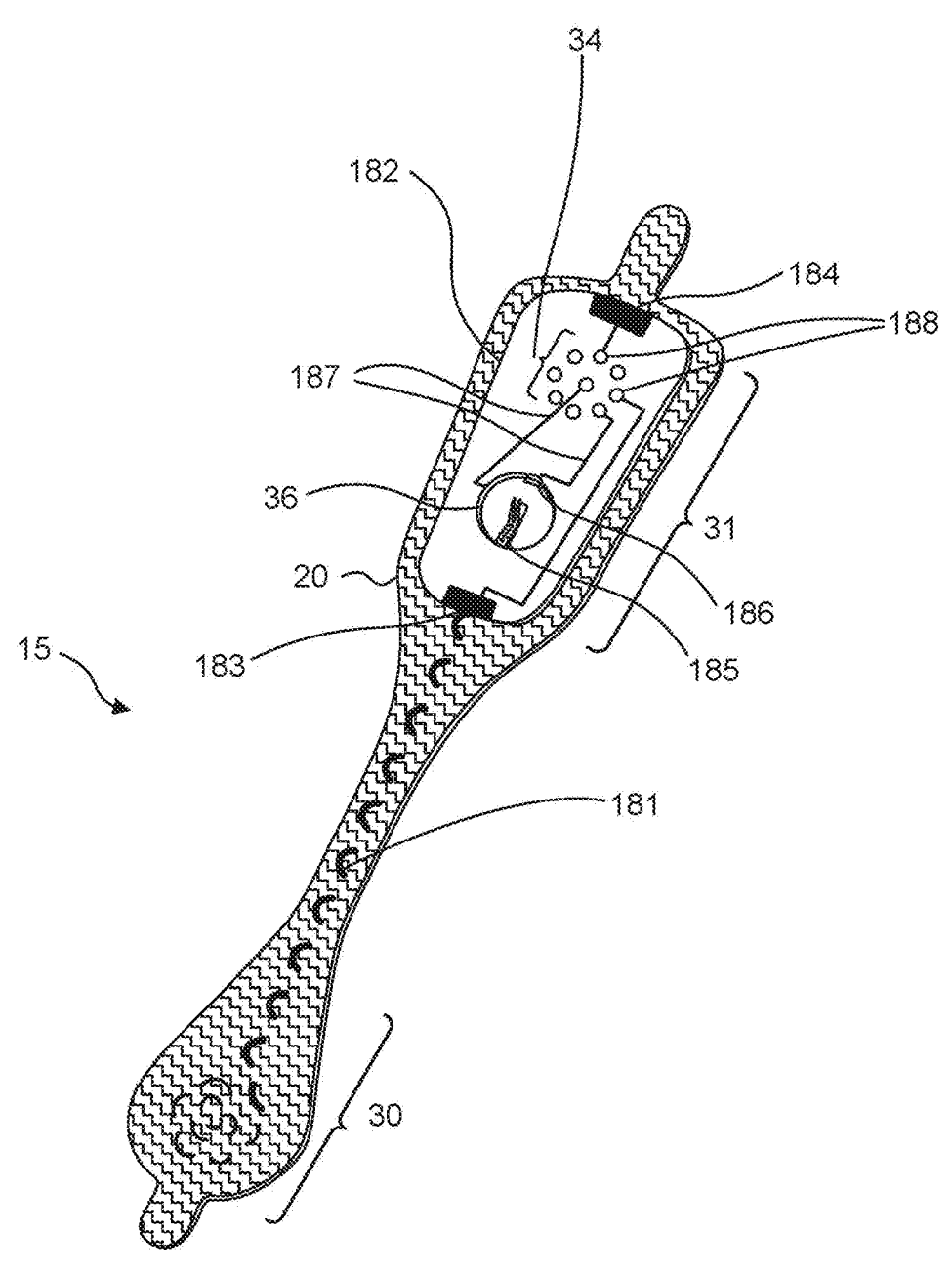
FIG. 17 is a perspective view of an extended wear electrode patch with a flexile wire electrode assembly in accordance with a still further embodiment.

The circuit trace and ECG electrodes components of the electrode patch 15 can be structurally simplified. In a still further embodiment, the flexible circuit 32 (shown in FIG. 5) and distal ECG electrode 38 and proximal ECG electrode 39 (shown in FIG. 6) are replaced with a pair of interlaced flexile wires. The interlacing of flexile wires through the flexible backing 20 reduces both manufacturing costs and environmental impact, as further described infra. The flexible circuit and ECG electrodes are replaced with a pair of flexile wires that serve as both electrode circuit traces and electrode signal pickups. FIG. 17 is a perspective view 180 of an extended wear electrode patch 15 with a flexile wire electrode assembly in accordance with a still further embodiment. The flexible backing 20 maintains the unique narrow "hourglass"-like shape that aids long term extended wear, particularly in women, as described supra with reference to FIG. 4. For clarity, the non-conductive receptacle 25 is omitted to show the exposed battery printed circuit board 182 that is adhered underneath the non-conductive receptacle 25 to the proximal end 31 of the flexible backing 20. Instead of employing flexible circuits, a pair of flexile wires are separately interlaced or sewn into the flexible backing 20 to serve as circuit connections for an anode electrode lead and for a cathode electrode lead.

To form a distal electrode assembly, a distal wire 181 is interlaced into the distal end 30 of the flexible backing 20, continues along an axial path through the narrow longitudinal midsection of the elongated strip, and electrically connects to the battery printed circuit board 182 on the proximal end 31 of the flexible backing 20. The distal wire 181 is connected to the battery printed circuit board 182 by stripping the distal wire 181 of insulation, if applicable, and interlacing or sewing the uninsulated end of the distal wire 181 directly into an exposed circuit trace 183. The distal wire-to-battery printed circuit board connection can be made, for instance, by back stitching the distal wire 181 back and forth across the edge of the battery printed circuit board 182. Similarly, to form a proximal electrode assembly, a proximal wire (not shown) is interlaced into the proximal end 31 of the flexible backing 20. The proximal wire is connected to the battery printed circuit board 182 by stripping the proximal wire of insulation, if applicable, and interlacing or sewing the uninsulated end of the proximal wire directly into an exposed circuit trace 184. The resulting flexile wire connections both establish electrical connections and help to affix the battery printed circuit board 182 to the flexible backing 20.

The battery printed circuit board 182 is provided with a battery compartment 36. A set of electrical pads 34 are formed on the battery printed circuit board 182. The electrical pads 34 electrically interface the battery printed circuit board 182 with a monitor recorder 14 when fitted into the non-conductive receptacle 25. The battery compartment 36 contains a spring 185 and a clasp 186, or similar assembly, to hold a battery (not shown) in place and electrically interfaces the battery to the electrical pads 34 through a pair battery leads 187 for powering the electrocardiography monitor 14. Other types of battery compartment are possible. The battery contained within the battery compartment 36 can be replaceable, rechargeable, or disposable.

In a yet further embodiment, the circuit board and non-conductive receptacle 25 are replaced by a combined housing that includes a battery compartment and a plurality of electrical pads. The housing can be affixed to the proximal end of the elongated strip through the interlacing or sewing of the flexile wires or other wires or threads.

The core of the flexile wires may be made from a solid, stranded, or braided conductive metal or metal compounds. In general, a solid wire will be less flexible than a stranded wire with the same total cross-sectional area, but will provide more mechanical rigidity than the stranded wire. The conductive core may be copper, aluminum, silver, or other material. The pair of the flexile wires may be provided as insulated wire. In one embodiment, the flexile wires are made from a magnet wire from Belden Cable, catalogue number 8051, with a solid core of AWG 22 with bare copper as conductor material and insulated by polyurethane or nylon. Still other types of flexile wires are possible. In a further embodiment, conductive ink or graphene can be used to print electrical connections, either in combination with or in place of the flexile wires.

Figure 18:
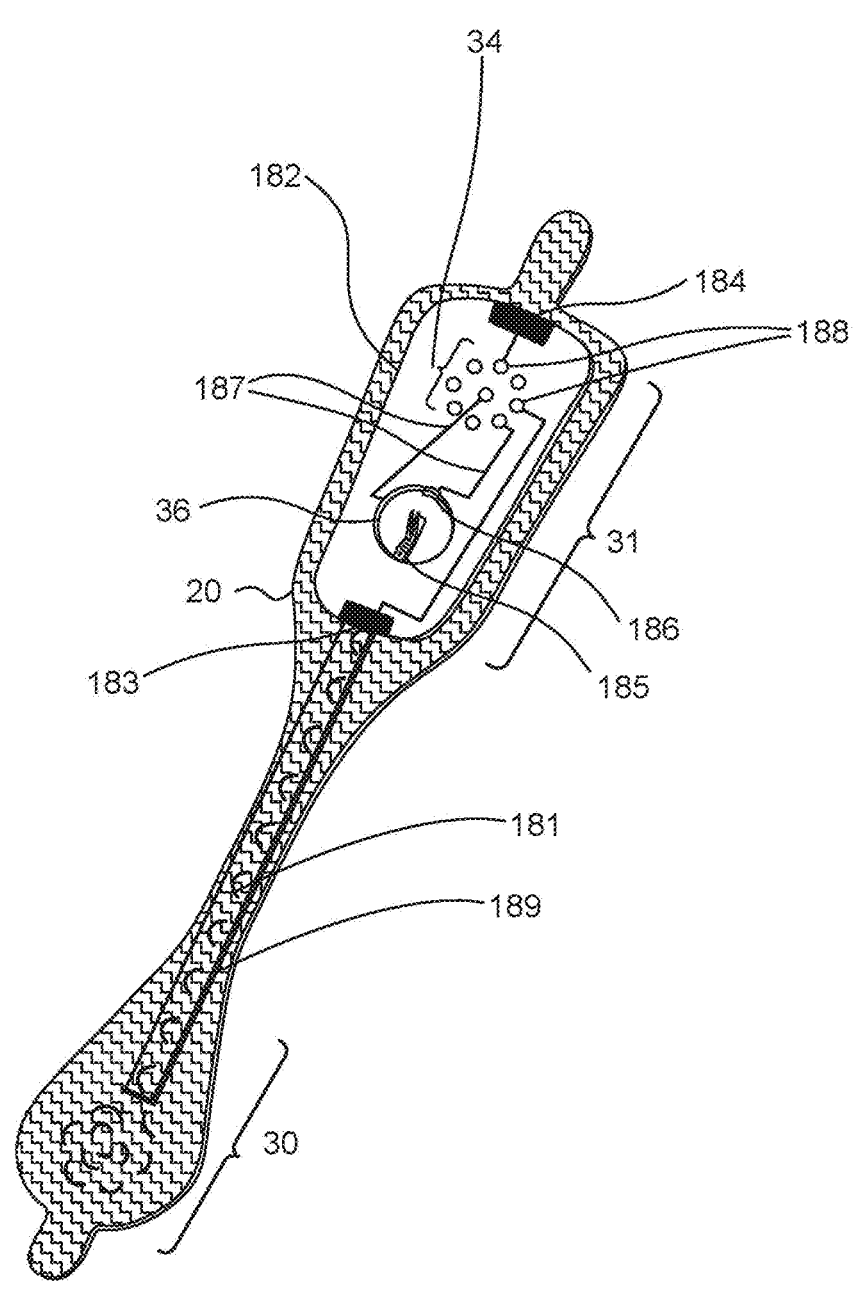
FIG. 18 is perspective view of the flexile wire electrode assembly from FIG. 17, with a layer of insulating material shielding a bare distal wire around the midsection of the flexible backing.

In a still further embodiment, the flexile wires are uninsulated. FIG. 18 is perspective view of the flexile wire electrode assembly from FIG. 17, with a layer of insulating material 189 shielding a bare uninsulated distal wire 181 around the midsection on the contact side of the flexible backing. On the contact side of the proximal and distal ends of the flexible backing, only the portions of the flexile wires serving as electrode signal pickups are electrically exposed and the rest of the flexile wire on the contact side outside of the proximal and distal ends are shielded from electrical contact. The bare uninsulated distal wire 181 may be insulated using a layer of plastic, rubber-like polymers, or varnish, or by an additional layer of gauze or adhesive (or non-adhesive) gel. The bare uninsulated wire 181 on the non-contact side of the flexible backing may be insulated or can simply be left uninsulated.

Figure 19:
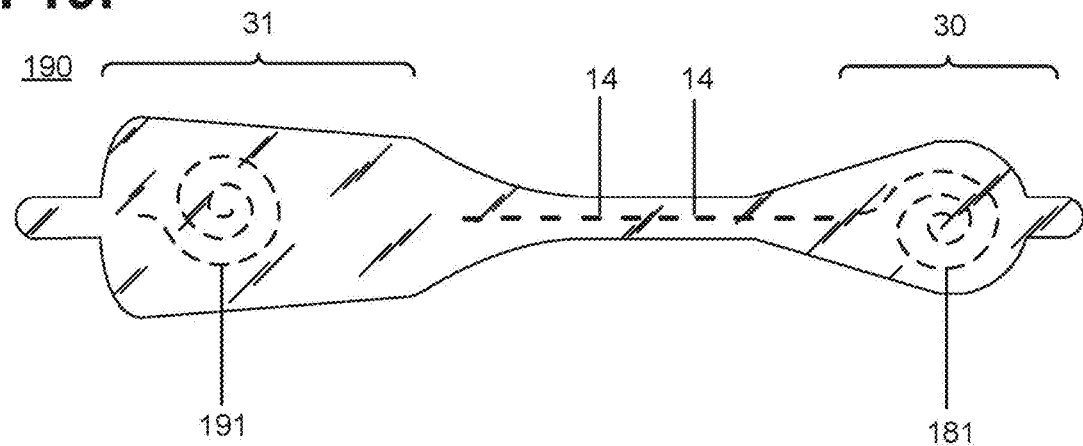
FIG. 19 is a bottom view of the flexile wire electrode assembly as shown in FIG. 17.

Both end portions of the pair of flexile wires are typically placed uninsulated on the contact surface of the flexible backing 20 to form a pair of electrode signal pickups. FIG. 19 is a bottom view 190 of the flexile wire electrode assembly as shown in FIG. 17. When adhered to the skin during use, the uninsulated end portions of the distal wire 181 and the proximal wire 191 enable the monitor recorder 14 to measure dermal electrical potential differentials. At the proximal and distal ends of the flexible backing 20, the uninsulated end portions of the flexile wires may be configured into an appropriate pattern to provide an electrode signal pickup, which would typically be a spiral shape formed by guiding the flexile wire along an inwardly spiraling pattern. The surface area of the electrode pickups can also be variable, such as by selectively removing some or all of the insulation on the contact surface. For example, an electrode signal pickup arranged by sewing insulated flexile wire in a spiral pattern could have a crescent-shaped cutout of uninsulated flexile wire facing towards the signal source.

In a still yet further embodiment, the flexile wires are left freely riding on the contact surfaces on the distal and proximal ends of the flexible backing, rather than being

Figure 20:
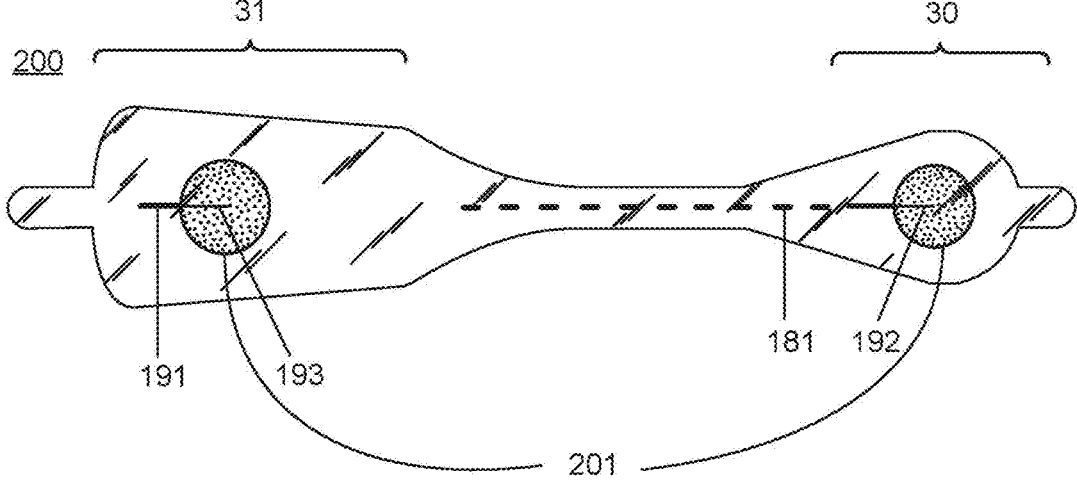
FIG. 20 is a bottom view of a flexile wire electrode assembly in accordance with a still yet further embodiment.

26 interlaced into the ends of the flexible backing 20. FIG. 20 is a bottom view 200 of a flexile wire electrode assembly in accordance with a still yet further embodiment. The distal wire 181 is interlaced onto the midsection and extends an exposed end portion 192 onto the distal end 30. The proximal wire 191 extends an exposed end portion 193 onto the proximal end 31. The exposed end portions 192 and 193, not shielded with insulation, are further embedded within an electrically conductive adhesive 201. The adhesive 201 makes contact to skin during use and conducts skin electrical potentials to the monitor recorder 14 (not shown) via the flexile wires. The adhesive 201 can be formed from electrically conductive, non-irritating adhesive, such as hydrocolloid.

Figure 21:
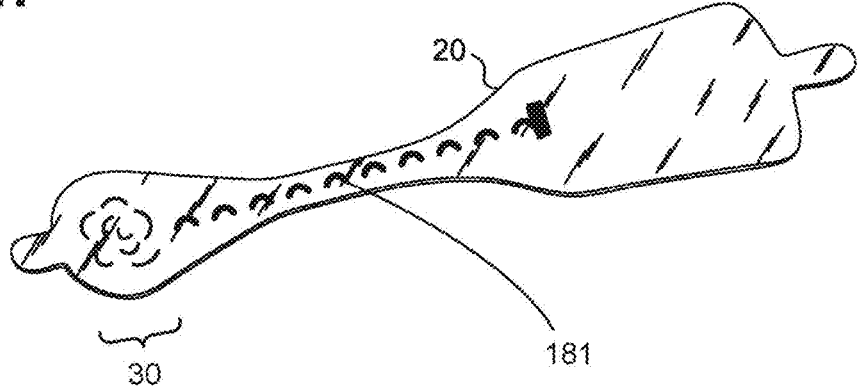
FIG. 21 is a perspective view showing the longitudinal midsection of the flexible backing of the electrode assembly from FIG. 17.

The distal wire 181 is interlaced or sewn through the longitudinal midsection of the flexible backing 20 and takes the place of the flexible circuit 32. FIG. 21 is a perspective view showing the longitudinal midsection of the flexible backing of the electrode assembly from FIG. 17. Various stitching patterns may be adopted to provide a proper combination of rigidity and flexibility. In simplest form, the distal wire 181 can be manually threaded through a plurality of holes provided at regularly-spaced intervals along an axial path defined between the battery printed circuit board 182 (not shown) and the distal end 30 of the flexible backing 20. The distal wire 181 can be threaded through the plurality of holes by stitching the flexile wire as a single "thread." Other types of stitching patterns or stitching of multiple "threads" could also be used, as well as using a sewing machine or similar device to machine-stitch the distal wire 181 into place, as further described infra. Further, the path of the distal wire 181 need not be limited to a straight line from the distal to the proximal end of the flexible backing 20.

While the invention has been particularly shown and described as referenced to the embodiments thereof, those skilled in the art will understand that the foregoing and other changes in form and detail may be made therein without departing from the spirit and scope.

What is claimed is:

1. A wearable electrocardiography monitor, comprising:
   a flexible backing having an adhesive surface, a midsection, a distal end, and a proximal end;
   a monitor recorder configured to output feedback to a patient, the monitor recorder comprising:
      a plurality of electrical contacts;
      a wireless transceiver;
      a feedback button disposed on a top surface of the monitor recorder, wherein the feedback button is configured to receive feedback from the patient; and
      electronic circuitry comprising an electrocardiographic front end circuit to sense electrocardiographic signals via a distal electrocardiography electrode and a proximal electrocardiography electrode;
   a receptacle fixed to the flexible backing, wherein the receptacle is configured to receive the monitor recorder, the receptacle comprising:
      a plurality of electrical pads configured to interface with the plurality of electrical contacts;
      a battery compartment configured to house a battery; and
   a flexible circuit comprising:
      an inline resistor;
      a proximal circuit trace, wherein the proximal circuit trace electrically couples the proximal electrocardiography electrode to a first electrical pad of the plurality of electrical pads; and a distal circuit trace, wherein the distal circuit trace electrically couples the distal electrocardiography electrode to a second electrical pad of the plurality of electrical pads.

2. The wearable electrocardiography monitor of claim 1, wherein the flexible backing includes an SpO$_2$ sensor.

3. The wearable electrocardiography monitor of claim 1, wherein the distal end and the proximal end are asymmetric about the mid-section.

4. The wearable electrocardiography monitor of claim 1, wherein the feedback button is circular and waterproof.

5. The wearable electrocardiography monitor of claim 1, wherein the feedback button is positioned on a side of the wearable electrocardiography monitor opposite to a further side on which the plurality of electrical contacts are positioned.

6. The wearable electrocardiography monitor of claim 1, wherein the battery is vertically aligned with the wireless transceiver.

7. The wearable electrocardiography monitor of claim 1, wherein the adhesive surface is only provided on the distal end and the proximal end.

8. The wearable electrocardiography monitor of claim 1, wherein the electrocardiographic signals are transmitted to at least one of a server, a client computer, or a mobile device via the wireless transceiver after the electrocardiographic signals are converted to a different format.

9. The wearable electrocardiography monitor of claim 1, wherein the distal end and the proximal end are rounded on respective outer edges.

10. A wearable electrocardiography monitor, comprising:
a backing having a distal end and a proximal end, wherein the backing is configured to adhere to skin of a patient via an adhesive surface on the distal end and the proximal end;
a monitor recorder comprising:
a plurality of electrical contacts extending from the monitor recorder;
electronic circuitry comprising an electrocardiographic front end circuit to sense electrocardiographic signals via a distal electrocardiography electrode and a proximal electrocardiography electrode; and
a feedback button disposed on a top surface of the monitor recorder, wherein the feedback button is configured to receive feedback from the patient;
a receptacle fixed to the backing, wherein the receptacle is configured to receive the monitor recorder, wherein, when the monitor recorder engages the receptacle, the plurality of electrical contacts contact a plurality of electrical pads on the receptacle;
a battery compartment configured to house a battery; and
a flexible circuit comprising:
an inline resistor;
a proximal circuit trace, wherein the proximal circuit trace electrically couples the distal electrocardiography electrode to a first electrical pad of the plurality of electrical pads; and
a distal circuit trace, wherein the distal circuit trace electrically couples the distal electrocardiography electrode to a second electrical pad of the plurality of electrical pads.

11. The wearable electrocardiography monitor of claim 10, wherein the wireless transceiver is configured to communicate with an external device via Wi-Fi, mobile phone communication standards, or Bluetooth.

12. The wearable electrocardiography monitor of claim 10, wherein the flexible backing includes an SpO$_2$ sensor.

13. The wearable electrocardiography monitor of claim 10, wherein the distal end and the proximal end are asymmetric about the mid-section.

14. The wearable electrocardiography monitor of claim 10,
wherein the battery is vertically aligned with the wireless transceiver;
wherein the battery is disposed between the monitor recorder and the skin of the patient;
wherein the wireless transceiver is configured to communicate at least a portion of the electrocardiographic signals; and
wherein the backing includes a mid-section having a first edge parallel to a second edge.

15. The wearable electrocardiography monitor of claim 10,
wherein the battery is disposed between the monitor recorder and the skin of the patient;
wherein the wireless transceiver is configured to communicate at least a portion of the electrocardiographic signals; and
wherein the backing includes a mid-section having a first edge parallel to a second edge.

16. The wearable electrocardiography monitor of claim 10,
wherein the battery is vertically aligned with the wireless transceiver;
wherein the wireless transceiver is configured to communicate at least a portion of the electrocardiographic signals; and
wherein the backing includes a mid-section having a first edge parallel to a second edge.

17. The wearable electrocardiography monitor of claim 10,
wherein the battery is vertically aligned with the wireless transceiver;
wherein the battery is disposed between the monitor recorder and the skin of the patient; and
wherein the backing includes a mid-section having a first edge parallel to a second edge.

18. The wearable electrocardiography monitor of claim 10,
wherein the battery is vertically aligned with the wireless transceiver;
wherein the battery is disposed between the monitor recorder and the skin of the patient; and
wherein the wireless transceiver is configured to communicate at least a portion of the electrocardiographic signals.

19. The wearable electrocardiography monitor of claim 10,
wherein the wireless transceiver is configured to communicate at least a portion of the electrocardiographic signals; and
wherein the backing includes a mid-section having a first edge parallel to a second edge.

20. The wearable electrocardiography monitor of claim 10,
wherein the battery is disposed between the monitor recorder and the skin of the patient; and
wherein the backing includes a mid-section having a first edge parallel to a second edge.

* * * * *